United States Patent
Soreq et al.

(10) Patent No.: US 6,475,998 B1
(45) Date of Patent: Nov. 5, 2002

(54) METHODS AND COMPOSITIONS FOR THE TREATMENT OF INJURY TO THE CENTRAL NERVOUS SYSTEM

(75) Inventors: Hermona Soreq, Jerusalem (IL); Shlomo Seidman, Gush Etzion (IL); Esther Shohami, Mevassert Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/380,532

(22) PCT Filed: Mar. 6, 1998

(86) PCT No.: PCT/US98/04503

§ 371 (c)(1),
(2), (4) Date: Nov. 12, 1999

(87) PCT Pub. No.: WO98/39486

PCT Pub. Date: Sep. 11, 1998

Related U.S. Application Data

(60) Provisional application No. 60/040,203, filed on Mar. 6, 1997.

(51) Int. Cl.[7] ................... A61K 48/00; C12Q 1/68; C07H 21/064; C12N 15/85
(52) U.S. Cl. ................. 514/44; 435/6; 435/69.1; 435/325; 435/366; 536/23.1; 536/24.5
(58) Field of Search .............. 435/6, 69.1, 91.1, 435/91.31, 440, 183, 195, 196, 325, 354, 366, 368, 375, 320.1; 514/44; 536/23.1, 24.31, 24.33, 24.5

(56) References Cited

U.S. PATENT DOCUMENTS 5,891,725 A * 4/1999 Soreq et al.
6,110,742 A * 8/2000 Soreq et al.
6,121,046 A * 9/2000 Soreq et al.

OTHER PUBLICATIONS

Branch, A.D. Tibs, vol. 23, Feb. 1998, pp. 45–50.*
Tanaka et al., Neurochemical Research, vol. 19, No. 2, Feb. 1994, pp. 117–122.*
Tanaka et al., Neurochemical Research, vol. 20, No. 6, Jun. 1995, pp. 663–667.*
Crooke, S.T. Chapter 1, in Antisense Research and Application, (ed. Stanley Crooke), Springer–Verlag, New York, 1998, pp. 1–50.*
Soreq et al. Proc. Natl. Acad. Sci. USA 91, 7907–7911, Aug. 1994.*

* cited by examiner

Primary Examiner—Andrew Wang
(74) Attorney, Agent, or Firm—Kohn & Associates

(57) ABSTRACT

The invention provides methods and pharmaceutical compositions thereof for treating injury to the central nervous system (CNS). The method includes administering to the CNS of a patient suffering from such an injury a therapeutically effective amount of an inhibitor of acetylcholinesterase (AChE) production immediately following the injury. The methods use as the inhibitor a synthetic nuclease resistant antisense oligonucleotide or ribozyme that is directed against an accessible domain of the AChE mRNA brain variant. The treatment downregulates AChE production and thereby activity. The injury to the CNS may be a head injury (closed or open), brain injury, or spinal cord trauma or other trauma to the CNS.

20 Claims, 6 Drawing Sheets

PROTEINS

HYDROPHILIC (TAILED)

mRNAs

H | E1 | E2 | E3 | E4 | E6 |

PI-LINKED (HYDROPHOBIC)

P, C | E1 | E2 | E3 | E4 | E5 | E6 |

READTHROUGH (PI-LINKED)

PR, C | E1 | E2 | E3 | E4 | I4 | E5 | E6 |

AUG — 0 — 1 — 2 — 3 kb

*Fig-4*

HYDROPHILIC (E1-4,6)

E4 → ← E6
H LLSAT▼DTLDEAERQWKAEFHRWSSYMVHWKNQFDHYSKQDRCSDL (SEQ ID NO:11)

PI-LINKED (E1-5)

E4 → ← E5
H LLSAT▼ASEAPSTCPGFTHGEAAPRPGLPLPLLLHCLLLLFLSHLRRL (SEQ ID NO:12)

READTHROUGH (E1-4, I4, E5)

E4 → ← I4 ← E5
H LLSAT▼GMQGPAGSGWEEGSGSPPGVTPLFSP (SEQ ID NO:13)

*Fig-5* ously. Yet, it has been nulation of AChE biosynthesis that is beneficial in the

METHODS AND COMPOSITIONS FOR THE TREATMENT OF INJURY TO THE CENTRAL NERVOUS SYSTEM

CROSS-REFERENCE TO RELATING APPLICATIONS

This application is a based on U.S. National Phase of PCT/US98/04503 filed Mar. 6, 1998, which claims the benefit of priority under 35 U.S.C. Section 119(e) of U.S. Provisional Patent Application No. 60/040,203 filed Mar. 6, 1997, which is incorporated herein by reference.

GRANT INFORMATION

Research in this application was supported in part by a grant from the United States Department of the Army (DAMD 17-86-C-6010). The government has certain rights in the invention.

GOVERNMENT SUPPORT

Research in this application was supported in part by U.S. Army Contract. THE U.S. government has a nonexclusive, nontransferable, irrevocable paid-up license to practice or have practiced this invention for or on its behalf as provided by the terms of the Contract DAMD17-97-1-7007 awarded by the U.S. Department of the Army.

BACKGROUND OF THE INVENTION

1. Field of the Invention

The present invention provides methods and compositions for treating trauma to the central nervous system (CNS). The present invention also provides methods and compositions for facilitating neuronal transplant.

2. Description of Related Art

The ACHE gene encoding the acetylcholine hydrolyzing enzyme, acetylcholinesterase (ACHE, EC 3.1.1.7), is expressed in muscle, nerve, hematopoietic cells, embryonic tissue and germ cells. ACHE maps to chromosome 7q22 and encodes the primary enzyme, acetylcholinesterase (AChE, E.C. 3.1.1.7), which terminates neurotransmission at synapses and neuromuscular junctions (NMJ). The text *Human Cholinesterases and Anticholinesterases* by Soreq and Zakut (Academic Press, Inc., 1993) provides a summation of the biochemical and biological background as well as the molecular biology of human cholinesterase genes. In addition Soreq et al. 1990; Seidman, et al. 1995; and Grifman et al., 1997 provide summations of various aspects of acetylcholinesterase biology. The text and references in their entirety are incorporated herein by reference.

Three alternative AChE-encoding mRNAs have been described in mammals. The dominant brain and muscle AChE found in NMJs (AChE-T) is encoded by an mRNA carrying exon E1 and the invariant coding exons E2, E3, and E4 spliced to alternative exon E6 (FIGS. 4–5). AChEmRNA bearing exons E1–4 and alternative exon ES encodes the glycolipid phosphatidylinositol (GPI)-linked form of AChE characteristic of vertebrate erythrocytes (AChE-H). An additional readthrough mRNA species retaining the intronic sequence I4 located immediately 3' to exon E4 was reported in rodent bone marrow and erythroleukemic cells and in various tumor cells lines of human origin.

In addition to its classical role as the enzyme responsible for acetylcholine hydrolysis, an increasing number of studies are suggesting a non-classical role for AChE in neurogenesis [reviewed in Robertson and Yu, 1993; Layer, 1995]. This is based on observations of intense patterns of AChE activity occurring transiently in many developing neural structures before synaptogenesis, or in locations which have no cholinergic synapses. In the vertebrate retina, four AChE-positive subbands have been described in the IPL [Marc, 1986; Hutchins, 1987], only two of which correspond to ChAT-positive subbands [Millar et al., 1985]. The other two are apparently not associated with cholinergic transmission. One possible explanation for these non-cholinergic AChE subbands is that they are related to neurite guidance. Several studies have demonstrated non-catalytic functions of AChE in the regulation of neurite outgrowth from embryonic neurons [Layer et al., 1992; Layer et al., 1993; Small et al., 1995].

It is proposed that AChE, and other cholinesterase-like molecules, are involved in cell-cell recognition. AChE displays homology to nervous system adhesion proteins such as neurotactin [de la Escalera, 1990; Darboux et al., 1996], gliotactin [Auld et al., 1995], and neuroligin [Ichtchenko et al., 1995]. Moreover, certain isoforms of AChE may possess an HNK-1 epitope that is commonly found on cell adhesion proteins [Bon et al., 1987].

Closed head injury (CHI) is a major cause of mortality and morbidity among young adults and an important risk factor in non familial Alzheimer's disease [French et al., 1991; Gentleman et al., 1993; Mayeux et al., 1995]. Following head trauma, disruption of the blood-brain-barrier contributes to the development of vasogenic edema. In addition, release of autodestructive factors leads to cytotoxicity and acute as well as delayed neuromotor and cognitive impairments [Caprusi and Levine, 1992; Hamm et al., 1996; Gennarelli, 1997]. The early phase of post-injury responses also includes a burst of released acetylcholine [Gorman et al., 1989] and elevated levels of intracellular calcium [Siesjo, 1993] in the brain. Pre-injury administration of the muscarinic antagonist scopolamine facilitates recovery from brain injury [Hamm et al., 1993], suggesting that rapid suppression of the early immediate intense stimulation mediated by acetylcholine released cholinergic hyperexcitation, during the first few post-injury minutes post-injury is therapeutically advantageous. However, other methods are needed that intervene at biologically significant steps so that recovery is assured and long-term risk factors for neurodegenerative diseases are avoided.

Acute cholinergic stimulation itself promotes a rapid and prolonged elevated overproduction (overexpression) of AChE [Friedman et al., 1996]. These elevated levels of AChE will act to brake the immediate phase of cholinergic hyperactivation. However, protracted overexpression of AChE will excessively suppress cholinergic neurotransmission.

Apart from its catalytic role, accumulated evidence establishes non-catalytic, neurite growth-promoting activities for AChE [Layer and Willbold, 1995, Koenigsberger et al., 1997; Sternfeld et al., 1998]. This suggests that elevated AChE levels might also promote a secondary phase of dendritic hypertrophy that could be important for short-term recovery from head injury such as CHI. Yet, it has been recently observed that extended overexpression of neuronal AChE in brain and spinal cord of transgenic mice promotes reduced dendritic branching, loss of dendritic spines (i.e. less synapses), and delayed, neuromotor and cognitive deficits [Beeri et al., 1995, 1997; Andres et al., 1997]. Together, these observations therefore raised the possibility that acute cholinergic stimulation following head trauma promotes an upregulation of AChE biosynthesis that is beneficial in the short term, but which causes long-term perturbations in the normal dendritic reorganization that takes place in the adult brain [Flood and Coleman, 1990, Arendt et al., 1995]. If so, the increased risk of AD among survivors of severe head injuries could be viewed as a delayed consequence of too long an exposure to AChE following injury and can potentially create imbalanced neurite extension and impaired targeting due to the neurite guidance role of AChE as described herein above. It would therefore be useful following head injury and any other injury to the central nervous system (CNS) to insure that an excess of AChE does not interfere with recovery, i.e. that a balance of AChE levels and timing is maintained. This is particularly critical in those patients which are already compromised in that their neural AChE levels are elevated due to biological, genetic or environmental factors.

It has been recently demonstrated [Chen et al, 1997A] that treatment of CHI with a brain specific inhibitor of anticholinesterase catalytic activity had a positive effect on short term recovery. However exposure to AChE enzymatic inhibitors itself activates a feedback loop leading to elevated levels of mRNA for AChE (AChEmRNA) [Friedman et al., 1996] and therefore this treatment has a potential for long term overexpression of AChE and subsequent development of neurodegenerative disease.

As with any therapy an appropriate model is required, either in vivo, ex vivo or in vitro. Since mice do not naturally overexpress AChE, Applicants have generated a unique transgenic mouse model for Alzheimer's Disease to serve this purpose [Beeri et al., 1995]. These genetically engineered mice overproduce human AChE in cholinergic brain cells providing a model of overexpressed AChE. Applicants' transgenic mice display age-dependent deterioration in cognitive performance as initially measured by a standardized swimming test for spatial learning and memory and a social recognition test. Since the excess acetylcholinesterase in the brains of these mice is derived from human DNA, it is a model for any intervention directed against human acetylcholinesterase protein and/or gene. This animal system and brain slices derived thereof, therefore provide the ability to test therapies by in vivo, ex vivo and in vitro means to restore balanced cholinergic signaling in the brain.

Transplantation of neural tissue into the mammalian CNS is a potential therapeutic treatment for neurological and neurodegenerative disorders including epilepsy, stroke, Huntington's diseases, head injury, spinal injury, pain, Parkinson's disease, myelin deficiencies, neuromuscular disorders, neurological pain, amyotrophic lateral sclerosis, Alzheimer's disease, and affective disorders of the brain. For example, fetal ventral mesencephalic tissue has been demonstrated to be a viable graft source in Parkinson's disease. [Lindvall et al., 1987; 1990; Bjorklund, 1992]. Likewise, fetal striatal tissue has been utilized successfully as graft material in Huntington's disease [Isacson et al., 1986; Sanberg et al., 1994].

Neurologically dysfunctional animals have been transplanted with non-fetal, non-neuronal cells/tissue. The major advantage of this type of transplantation protocol is that the graft source is not a fetal source and, thereby, circumvents the ethical and logistical problems associated with acquiring fetal tissue [Bjorklund and Stenevi, 1985; Lindvall et al., 1987]. It would be useful to be able to also use neural grafts of non-fetal neuronal cells and to improve the graft integration (form connections) with the CNS of the recipient (i.e. the host) as has been shown by Wictorin et al. [1990].

SUMMARY OF THE INVENTION

According to the present invention, a method of treating injury to the central nervous system (CNS) is provided. The method includes administering to the CNS of a patient suffering from such an injury a therapeutically effective amount of an inhibitor of acetylcholinesterase production immediately following the injury. The treatment downregulates acetylcholinesterase production and thereby activity. The injury to the CNS may be a head injury (closed or open) or a spinal cord trauma or other trauma to the CNS.

The method uses as the inhibitor of acetylcholinesterase production a synthetic nuclease resistant antisense oligodeoxynucleotide or a ribozyme wherein they are directed against an accessible domain of the AChEmRNA brain variant and pharmaceutical compositions thereof. In an embodiment the inhibitor is at least one synthetic nuclease resistant antisense oligodeoxynucleotide selected from 5'ACGCTTTCTTGAGGC 3' (SEQ ID No:1),
    5'GGCACCCTGGGCAGC 3' (SEQ ID No:2),
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

The method further includes the inhibitor being administered a second time following monitoring of the patient and determining upon magnetic resonance imaging (MRI), that c-fos activity is still seen.

The present invention further provides a method of facilitating transplantation of neuronal cells to the CNS by administering to the patient a therapeutically effective amount the acetylcholinesterase inhibitor of production or pharmaceutical composition thereof at the time of transplant. The neuronal cells to be transplanted can be neurons of fetal origin, neurons of adult origin or a neuronal cell line and can be genetically modified to produce a noncatalytic brain specific variant (E6) of acetylcholinesterase under control of an inducible promoter.

The present invention also provides a method of improving hippocampal neuron survival following injury to the central nervous system by administering to a patient suffering from such an injury a therapeutically effective amount of an inhibitor of acetylcholinesterase production to the central nervous system of the patient immediately following the injury. The injury to the central nervous system may be a closed or open head injury or a spinal cord trauma.

The method uses as the inhibitor of acetylcholinesterase production a synthetic nuclease resistant antisense oligodeoxynucleotide or a ribozyme directed against an accessible domain of the AChEmRNA brain variant or a pharmaceutical composition thereof. In an embodiment the inhibitor is at least one synthetic nuclease resistant antisense oligodeoxynucleotide selected from 5'ACGCTTTCTTGAGGC 3' (SEQ ID No:1),
    5'GGCACCCTGGGCAGC 3' (SEQ ID No:2),
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

The present invention provides a pharmaceutical or medical composition for the treatment of injury to the central nervous system comprising as active ingredient at least one inhibitor of acetylcholinesterase in a physiologically acceptable carrier or diluent. The active ingredient can be a synthetic nuclease resistant antisense oligodeoxynucleotide or a ribozyme directed against an accessible domain of the AChEmRNA brain variant or a combination thereof.

In an embodiment the synthetic nuclease resistant antisense oligodeoxynucleotides are selected from the group consisting of 5'ACGCTTTCTTGAGGC 3' (SEQ ID No:1),
    5'GGCACCCTGGGCAGC 3' (SEQ ID No:2)
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5), 5'TAGCGTCTACCACCCCTGAC 3' (SEQ ID No:6),
5'TCTGTGTTATAGCCCAGCCC 3' (SEQ ID No:7), and
5'GGCCTGTAACAGTTTATTT 3' (SEQ ID No:8).

DESCRIPTION OF THE DRAWINGS

Other advantages of the present invention will be readily appreciated as the same becomes better understood by reference to the following detailed description when considered in connection with the accompanying drawings wherein:

FIG. 4 is a schematic diagram of the three splice variants of AChE.

FIG. 5 is a schematic diagram showing the amino acid sequences of human (H) AChE variants from the end of E4 to the end of the protein in the three variants, E1–4,6, E1–5, E1–4-I4-E5 (readthrough).

DETAILED DESCRIPTION OF THE INVENTION

Figure 1:
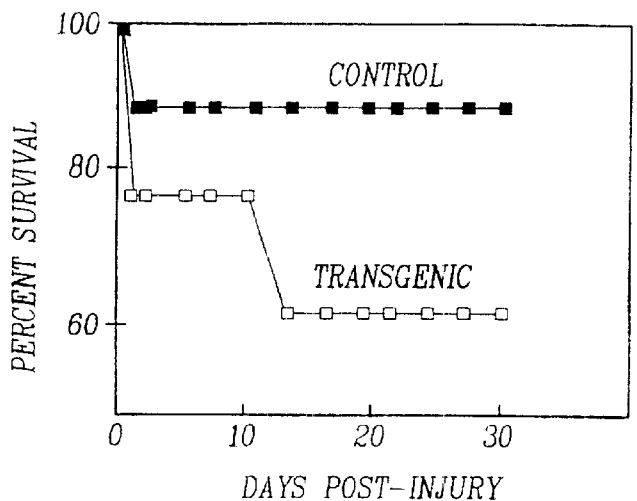
FIG. 1 is a graph showing high mortality among AChE transgenic mice following head injury. Four-month-old control FVB/N and AChE transgenic mice were subjected to unilateral closed head injury and monitored for recovery for up to 30 days. Presented are percentages of mice surviving the injury at the noted days following trauma.

The present invention provides a method and use of treating trauma injury to the central nervous system (CNS) in a patient, including head injury (open and closed) and spinal cord injury (generally compression type). The patient with such an injury is administered a therapeutically effective amount of an inhibitor of acetylcholinesterase production immediately following the injury. This administration downregulates acetylcholine esterase production and in so doing the activity is reduced. Already synthesized AChE is still available for use and as discussed herein, the noncatalytic properties of the molecule are involved in the healing process, but overproduction of protein which has subsequent long-term harmful effects is prevented.

The administration is generally within four hours of the injury when it is known that the blood-brain-barrier is still open in response to the trauma [Chen et al, 1997A). Administration is particularly critical for those patients which are already compromised in that their neural AChE levels are elevated due to biological, genetic or environmental factors.

For example applicants have demonstrated that in stressed mammalian brain there is enhanced AChE production for at least 80 hours in the cortex following stress. Environmental exposure to anti-cholinesterase intoxications, anti-cholinesterase poisons as for example many agricultural and household pesticides including organophosphorous and carbamate agents as well as medical therapeutics [Loewenstein-Lichtenstein et al., 1995] can result in AChE overproduction through a feedback loop [Friedman et al., 1996]. Further, the allelic variants at the ACHE gene level can affect the production level of AChE.

In an emergency trauma situation identifying those patients who are overexpressing AChE would be impractical. Applicants have however unexpectedly found, as shown in the Examples herein, that patients who are not overexpressing AChE due to genetic, medical or environmental factors also benefit from the method of the present invention in that this method improves the survival of hippocampal neurons without adverse effects from the downregulation of AChE production. Those patients with overexpressed AChE levels in addition to improved survival of hippocampal neurons benefit from the method of the present invention by having an increased survival, and reduction of feedback loops of AChE production as well as improved resolution of short-term effects of the injury.

The present invention also provides a method of improving hippocampal neuron survival following injury to the CNS by administering to the CNS of a patient suffering from such an injury a therapeutically effective amount of an inhibitor of acetylcholinesterase production immediately following the injury.

The inhibitor of acetylcholinesterase production is generally a synthetic nuclease resistant antisense oligodeoxynucleotide (AS-ODN) or ribozyme directed against an accessible domain of the AChEmRNA brain variant. The sequence is selected such that it is targeted to a splice variant of the AChEmRNA that is active/predominant in the central nervous system thereby reducing or eliminating the AS-ODN activity in other tissues. The target sequence is selected so as to be accessible to the AS-ODN and unique to the splice variant in the CNS.

In an embodiment where AS-ODN are used, at least one synthetic nuclease resistant AS-ODN is selected from:

5'ACGCTTTCTTGAGGC 3' (SEQ ID No:1),

5'GGCACCCTGGGCAGC 3' (SEQ ID No:2)

5'CCACGTCCTCCTGCACCGTC 3' (SEQ ID No:3),

5'ATGAACTCGATCTCGTAGCC 3' (SEQ ID No:4),

5'GCCAGAGGAGGAGGAGAAGG 3' (SEQ ID No:5),

5'TAGCGTCTACCACCCCTGAC 3' (SEQ ID No:6),

5'TCTGTGTTATAGCCCAGCCC 3' (SEQ ID No:7), or

5'GGCCTGTAACAGTTTATTT 3' (SEQ ID No:8).

SEQ ID No:1 is directed against the human ACHE sequence starting at position 1119 (for numbering of nucleotides see Soreq et al, 1990). SEQ ID No:2 is directed against the human ACHE sequence starting at position 1507. SEQ ID Nos:3 and 4 are located in Exons 2 and 3, SEQ ID Nos: 5 and 6 are located near the initiation site in Exon 2 and SEQ ID Nos:7 and 8 are located in Exon 6.

The term "oligonucleotide" refers to an oligomer or polymer of nucleotide or nucleoside monomers consisting of naturally occurring bases, sugars and intersugar (backbone) linkages. The term also includes modified or substituted oligomers comprising non-naturally occurring monomers or portions thereof, which function similarly. Incorporation of substituted oligomers is based on factors including enhanced cellular uptake, or increased nuclease resistance and are chosen as is known in the art. The entire oligonucleotide or only portions thereof may contain the substituted oligomers.

Antisense intervention in the expression of specific genes can be achieved by the use of synthetic antisense oligonucleotide sequences [for recent reports see Lefebvre-d'Hellencourt et al, 1995; Agrawal, 1996; Lev-Lehman et al, 1997]. Antisense oligonucleotide sequences may be short sequences of DNA, typically 15–30 mer but may be as small as 7 mer [Wagner et al, 1996] designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation [Calabretta et al, 1996]. In that case, RNase H will cleave the RNA component of the duplex and can potentially release the AS to further hybridize with additional molecules of the target RNA. An additional mode of action results from the interaction of AS with genomic DNA to form a triple helix which may be transcriptionally inactive.

Antisense induced loss-of-function phenotypes related with cellular development were shown for the glial fibrillary acidic protein (GFAP), for the establishment of tectal plate formation in chick [Galileo et al., 1992] and for the N-myc protein, responsible for the maintenance of cellular heterogeneity in neuroectodermal cultures (ephithelial vs. neuroblastic cells, which differ in their colony forming abilities, tumorigenicity and adherence) [Rosolen et al., 1990; Whitesell et al, 1991]. Antisense oligonucleotide inhibition of basic fibroblast growth factor (bFgF), having mitogenic and angiogenic properties, suppressed 80% of growth in glioma cells [Morrison, 1991] in a saturable and specific manner.

Nuclease resistance, where needed, is provided by any method known in the art that does not substantially interfere with biological activity of the antisense oligodeoxynucleotides or ribozymes as needed for the method of use and delivery [Iyer et al., 1990; Radhakrishnan, et al., 1990; Eckstein, 1985; Spitzer and Eckstein, 1988; Woolf et al., 1990; Shaw et al., 1991]. Modifications that can be made to antisense oligonucleotides or ribozymes in order to enhance nuclease resistance include modifying the phosphorous or oxygen heteroatom in the phosphate backbone, short chain alkyl or cycloalkyl intersugar linkages or short chain heteroatomic or heterocyclic intersugar linkages. These include preparing 2'-fluoridated, O-methylated, methyl phosphonates, phosphorothioates, phosphorodithioates and morpholino oligomers. In a non-limiting embodiment it is provided by having phosphorothioate bonds linking between the four to six 3'-terminus nucleotide bases. Alternatively, phosphorothioate bonds link all the nucleotide bases. Phosphorothioate antisense oligonucleotides do not normally show significant toxicity at concentrations that are effective and exhibit sufficient pharmacodynamic half-lives in animals [Agarwal et al., 1996] and are nuclease resistant. Alternatively the nuclease resistance for the AS-ODN can be provided by having a 9 nucleotide loop forming sequence at the 3'-terminus having the nucleotide sequence CGC-GAAGCG (SEQ ID No:10). The use of avidin-biotin conjugation reaction can also be used for improved protection of AS-ODNs against serum nuclease degradation [Boado and Pardridge, 1992]. According to this concept the AS-ODN agents are monobiotinylated at their 3'-end. When reacted with avidin, they form tight, nuclease-resistant complexes with 6-fold improved stability over non-conjugated ODNs.

Studies of others have shown extension in vivo of AS-oligodeoxynucleotides [Agarwal et al., 1991]. This process, presumably useful as a scavenging mechanism to remove alien AS-oligonucleotides from the circulation depends on the existence of free 3'-termini in the attached oligonucleotides on which the extension occurs. Therefore partial phosphorothioate, loop protection or biotin-avidin at this important position should be sufficient to ensure stability of these AS-oligodeoxynucleotides.

The present invention also includes use of all analogues of, or modifications to, an oligonucleotide of the invention that does not substantially affect the function of the oligonucleotide or ribozyme. Such substitutions may be selected, for example, in order to increase cellular uptake or for increased nuclease resistance as is known in the art. The term may also refer to oligonucleotides or ribozymes which contain two or more distinct regions where analogues have been substituted.

The nucleotides can be selected from naturally occurring or synthetically modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, morpholino polymer backbones [U.S. Pat. No. 5,034,506], cyclic backbones, or acyclic backbones, sugar mimetics or any other modification including which can improve the pharmacodynamics properties of the oligonucleotide.

The synthetic nuclease resistant antisense oligodeoxynucleotides or ribozymes of the present invention can be synthesized by any method known in the art. For example, an Applied Biosystems 380B DNA synthesizer can be used. Final purity of the oligonucleotides or ribozymes is determined as is known in the art.

In addition to, or substituted for, an antisense sequence as discussed herein above, ribozymes may be utilized for suppression of gene function. This is particularly necessary in cases where antisense therapy is limited by stoichiometric considerations [Sarver et al., 1990]. Ribozymes can then be used that will target the same sequence. Ribozymes are RNA molecules that possess RNA catalytic ability [see Cech for review] that cleave a specific site in a target RNA. The number of RNA molecules that are cleaved by a ribozyme is greater than the number predicted by stoichiochemistry. [Hampel and Tritz, 1989; Uhlenbeck, 1987]. Therefore, the present invention also allows for the use of the ribozyme sequences targeted to an accessible domain of the AChEm-RNA brain variant and containing the appropriate catalytic center. The ribozymes are made and delivered as discussed herein below. The ribozymes may be used in combination with the antisense sequences.

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4–5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). The ribozyme type utilized in the present invention is selected as is known in the art. Hairpin ribozymes are now in clinical trial and are the preferred type. In general the ribozyme is from 30–100 nucleotides in length.

The present invention also discloses a pharmaceutical or medical composition for the treatment of injury to the central nervous system comprising as active ingredient at least one inhibitor of acetylcholinesterase in a physiologically acceptable carrier or diluent. They may be used individually or in combination. In an embodiment where AS-ODN are used, at least one synthetic nuclease resistant AS-ODN is selected, but combinations can be used, from:
5'ACGCTTTCTTGAGGC 3' (SEQ ID No:1),
5'GGCACCCTGGGCAGC 3' (SEQ ID No:2)
5'CCACGTCCTCCTGCACCGTC 3' (SEQ ID No:3),
5'ATGAACTCGATCTCGTAGCC 3' (SEQ ID No:4),
5'GCCAGAGGAGGAGGAGAAGG 3' (SEQ ID No:5),
5'TAGCGTCTACCACCCCTGAC 3' (SEQ ID No:6),
5'TCTGTGTTATAGCCCAGCCC 3' (SEQ ID No:7), or
5'GGCCTGTAACAGTTTATTT 3' (SEQ ID No:8).

The AS-ODN, ribozymes or pharmaceutical compositions thereof is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to changes in levels of AChE in the CNS, or improvement or elimination of symptoms and other indicators as are selected as appropriate measures by those skilled in the art. In general the dose is in the range of 1 to 4 mg/kg body weight with 2.5 as a non-limiting preferred dose.

For specific delivery within the CNS intrathecal delivery can be used with, for example, an Ommaya reservoir. U.S. Pat. No. 5,455,044 provides for use of a dispersion system for CNS delivery or see U.S. Pat. No. 5,558,852 for a discussion of CNS delivery. In addition, pharmacological formulations that cross the blood-brain barrier can be administered [Betz et al., 1994; Brem et al., 1993]. Such formulations can take advantage of methods now available to produce chimeric molecules in which the present invention is coupled to a brain transport vector allowing transportation across the barrier [Pardridge, et al., 1992; Pardridge, 1992; Bickel, et al., 1993].

The method of the present invention can include administration of a further dose of the inhibitor of production of ACHE. Generally this second dose is administered following monitoring of the patient with magnetic resonance imaging (MRI) if c-fos activity is still seen within two days of the trauma. MRI reflects general metabolism levels in the brain and c-fos upregulates those levels. As long as the general metabolism levels are up, the AChE production is continuing and must be downregulated to prevent overproduction of AChE and its long-term harmful sequela.

The present invention further provides a method of facilitating transplantation of neuronal tissue to the CNS of a patient in need of such transplantation. The patient can be afflicted with neurological and neurodegenerative disorders including epilepsy, stroke, Huntington's disease, head injury, spinal injury, pain, Parkinson's disease, myelin deficiencies, neuromuscular disorders, neurological pain, amyotrophic lateral sclerosis, Alzheimer's disease, and affective disorders of the brain all of which may benefit from such transplantation as is known in the art.

The neuronal cells can be of fetal or adult origin or neuronal cell lines and can be genetically modified as for example as set forth in U.S. Pat. No. 5,082,670 to Gage et al and incorporated in its entirety by reference.

Transplanted neuronal cells (graft) must integrate into the host and as part of this integration need to extend neurites into the brain. Therefore the noncatalytic functions of AChE can be beneficial for graft integration (see Example 3 herein). However, overexpression of AChE should be elicited in the host (graft recipient) brain as discussed herein for head trauma since the transplantation event itself is a trauma to the brain. This increase throughout the brain can be deleterious. During the transplantation process itself the same cascade of events which initiates with AChE overproduction and which becomes active in a CHI can be activated. This causes long-term damage to neurons. While therapeutic techniques associated with the transplantation do work to control this aspect additional protocols would be useful. As discussed herein, the catalytic activity of the host brain AChE must be muted to allow for cholinergic excitation during the initial post-transplant period but the noncatalytic functions must be available for dendritic branching and neurite guidance (integration) [Layer et al., 1992; Layer et al., 1993; Small et al., 1995].

The method of the present invention therefore provides for the treatment at transplantation with a therapeutically effective amount of an inhibitor of production of acetylcholine esterase as described hereinabove for treatment of CNS injury to the host brain. This treatment is particularly necessary in those patients who are overexpressers of AChE in the CNS. For example, the neurodegenerative processes associated with Parkinson's Disease (PD) reflect an existing overproduction of AChE. Over 50% of PD patients receive anticholinesterase therapy and are subject to the feedback loop production of AChE as described herein. Therefore, PD patients represent patients who are at higher risk for AChE overexpression.

As shown in the Examples the noncatalytic functions of AChE are one factor necessary for neuritic extension in the brain. Therefore the noncatalytic functions of AChE are necessary at the proper level for graft integration, however overexpression of AChE must also be prevented for long term survival. In order to provide for this, the method of the present invention provides for the step of genetically modifying the neuronal cells, as for example as set forth in U.S. Pat. No. 5,082,670 to Gage et al, to produce under an inducible expression system a cDNA for a catalytically inactive AChE brain variant form. Therefore the transplanted neuronal cells can be induced to produce the necessary level of noncatalytic AChE to mediate neurite outgrowth. In general, the inhibitor of AChE production is provided following, or at the end of, transplantation surgery. The noncatalytically active AChE variant is induced for 2–6 days following the surgery with 4 days a preferred time course. However, monitoring of graft integration via MRI for example may indicate the necessity for additional courses of expression.

The vectors are made as known in the art such as described by U.S. Pat. Nos. 5,681,731; 5,670,488; 5,585,254; 5,686,278. The inducible promoter is selected to be compatible with brain chemistry and passage of the inducer through the blood-brian-barrier (see U.S. Pat. Nos. 5,538,885 and 5,698,443 for examples of methods to select such expression systems). The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

As shown in the Examples herein, by comparing normal mice with transgenic mice overexpressing AChE in cholinergic brain neurons, a trilateral correlation was demonstrated between induced overexpression of AChE, dendrite outgrowth, and clinical recovery from brain injury. However, these findings indicate that the processes mediating recovery from head trauma include those very elements that occasion a predisposition to late-onset neurodegenerative disease. In the transgenic model used herein, acetylcholine release following trauma initiates a critical, early immediate phase of injury response involving transient cholinergic hyperfunction. The first few minutes of this response can be harmful, which is why pre-injury, but not post-injury, treatment with scopolamine proved beneficial [Hamm et al. 1993, Dixon et al., 1994]. In contrast, during the next few hours post-injury, cholinergic hyperexcitation is required for survival. The acetylcholine deficit imposed by transgenic overexpression of AChE therefore explains the high mortality among ACHE transgenic mice during the first phase post injury and hence the use of AChE inhibitors of production as set forth in the present invention to treat head injury. There is a short and early therapeutic window for effective use of anticholinesterases in treating head trauma.

Applicants recently observed that brief cholinergic stimulation promotes a c-Fos mediated induction of AChE in stressed mice and in hippocampal brain slices [Friedman et al., 1996]. The heightened cholinergic activity, as well as the oxidative stress which follows CHI [Shohami et al., 1997] would also be expected to activate c-Fos and induce AChE production. The data in the Examples herein indicate that AChE induced in the wake of head trauma promotes a secondary phase of recovery that recruits both the catalytic and non-catalytic activities of the enzyme. While elevated levels of acetylcholine hydrolyzing activity (enzymatic activity) would terminate the acute phase of hyperactivity, elevated levels of AChE protein would initiate a process of neurite outgrowth/branching via the non-catalytic morphogenic activities of the polypeptide.

Dendrites have been shown capable of rapid growth during both normal embryonic development and adult life [Purves and Hadley, 1985; Flood and Coleman, 1990] and following injury [Caceres and Steward, 1983]. A phase of dendritic outgrowth would serve to reestablish neural connectivity disrupted by the injury and could play an important role in determining the rate and extent of neurological recovery and neuronal survival. The high incidence of neuron death in the hippocampus of transgenic mice may hence reflect their preinjury deficit in dendrite branching, impairing the reconstruction of lost synaptic connections during the first few days post-injury. Impaired dendrite branching is one of the features that distinguishes normal aged from demented human brains [Buell and Coleman, 1979] and is considered to reflect their inability to compensate for neurons lost during aging. These findings thus indicate that neurite outgrowth following head injury has a neuroprotective value, which points to an important role for the noncatalytic functions of AChE in mediating secondary responses to head trauma.

Elevated levels of AChEmRNA and expanded dendrite fields were observed for weeks after CHI in both control and transgenic mice. These data show that a single event of traumatic injury may carry long-term cellular and molecular consequences for the brain, especially since uninjured ACHE transgenic mice develop late-onset, progressive cognitive and neuromotor deficits. These have been attributed to chronic overexpression of AChE in cholinergic brain and spinal cord neurons. Moreover, the delayed-onset appearance of symptoms resembling Alzheimer's disease in these transgenic mice was correlated with abnormal dendrite branching (Beeri et al., 1997], suggesting that persistent overexpression of AChE is detrimental to long-term synaptic structure and function. In the traumatized brain, long-term ACHE overexpression is therefore a major factor for the increased risk of Alzheimer's disease. The present invention provides a method to contain injury-induced overexpression of AchE to the minimal period necessary to suppress hypercholinergic responses and to promote healthy rebuilding of neural networks. In the method of the present invention, cholinesterase inhibitors of production are used to block production of the enzyme to allow recovery and in particular to prevent hippocampal neuronal death and other long-term sequela. Antisense oligonucleotides preventing synthesis of the protein are used for this as described herein (and see also Grifman and Soreq, 1997).

A recent study demonstrates that the k variant of the AChE-homologous enzyme butyrylcholinesterase, with reduced potential for inhibitor scavenging, adds to the increased risk for Alzheimer's disease associated with the ApoE4 genotype [Lehman et al., 1997]. Also, ApoE-null mice display reduced ChAT activity, impaired response to cholinergic agonists, and deficient working memory (Gordon et al., 1995) in addition to high vulnerability to brain injury (Chen et al., 1997b). This indicates that the ApoE associated risk for AD involves a cholinergic component and suggests that both genetic and environmental factors regulating AChE expression should be added to the list of risk factors for delayed onset neurodegenerative diseases. The variability in individual susceptibilities to cholinesterase inhibitors used as pesticides and as medical therapeutics [Loewenstein-Lichtenstein et al., 19951] further indicates that allelic polymorphism affecting the ACHE and BCHE genes can modulate levels of AChE expression. Additionally, exposure to AChE inhibitors itself activates a feedback loop leading to elevated levels of AChEmRNA [Friedman et al., 1996] strengthens the concept that both environmental and genetic factors contribute to AChE levels in the brain and therefore affect an individual's recovery from head trauma.

The pre-injury differences in AChEmRNA labeling and Golgi staining observed between AChE transgenic and control mice prior to the injury equalized post-injury. This demonstrates the natural processes that exist to overcome preexisting differences in ACHE load in the brain, at least to some extent. However, the delayed neurological recovery of transgenic mice throughout the 30 day follow-up period suggests that congenital differences in ACHE gene expression could pre-determine the progress of adult recovery from CHI. This is perhaps due to early secondary differences in the expression of other genes. For example, suppressed levels of neurexin Iβ in the brain of AChE transgenic mouse embryos [Andres et al., 1997] may alter circuitry formation in the developing brain [Puschel and Betz, 1996], thus increasing its vulnerability to subsequent insults. Basal AChE expression levels and preexisting deficiencies in dendrite branching therefore represent indeterminable but important factors in the prognosis of trauma patients. Any treatment protocol must take these considerations into account as has been done in the method of the present invention.

The observation that AChE is induced following both acute psychological stress and head trauma experiences suggests that AChE might serve as a general stress-response element in the CNS. Indeed, mammalian ACHE promoters [Ben Aziz et al., 1993] contain binding sites for multiple transcription factors known to be induced under various stress situations: STRE, c-fos, CRE, GAGA and MTF1 [Martinez-Pastor et al., 1996]. Moreover, pre-injury adrenalectomy, attenuating stress responses, facilitated recovery from CHI [Shohami et al., 1995b]. The valuable role that AChE can play in short to intermediate range recovery processes is therefore understandable in terms of both catalytic and non-catalytic activities of the protein-attenuation of neuronal hyperexcitability following trauma, and facilitation of neural plasticity essential for restoration of damaged or lost networks of communication. Moreover, the beneficial effects of a single administration of ENA 713 (AChE inhibitor Rivastigmine) (Example 4) on the long-term outcome of closed head injury in rats suggests that anticholinesterase treatment of head trauma may operate on two levels:

1. improved cholinergic transmission during the acute phase of recovery;
2. stimulation of dendrite outgrowth during the secondary phase of recovery through augmentation of AChE overexpression.

It is essential to keep in mind, however, that recruitment of AChE for processes driving short-term recovery from traumatic insults to the brain must be finely tuned to avert long-term, delayed neuropathological sequelae as shown by the present invention.

The above discussion provides a factual basis for the method of the present invention in treating injury to the CNS and facilitating neuronal transplants. The methods used with and the utility of the present invention can be shown by the following non-limiting examples and accompanying figures.

EXAMPLES

General Method

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) was carried out generally as in *PCR Protocols: A Guide To Methods And Applications*, Academic Press, San Diego, Calif. (1990).

Reactions and manipulations involving other nucleic acid techniques, unless stated otherwise, were performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference.

Synthesis of Antisense Oligodeoxynucleotides: Oligodeoxynucleotides were synthesized on an Applied Biosystems 380B DNA synthesizer using phosphoramidites from the same company according to the manufacturer's instructions. They were purified by reverse phase HPLC on a Waters dual pump 6000A system in combination with a Waters automated gradient controller and a model 481 UV spectrophotometer operated at 260 nm with the 5'-protecting dimethoxytrityl group still attached to the oligodeoxynucleotides. This was removed by standard treatment with 80% aqueous acetic acid. The oligodeoxynucleotides obtained were checked for purity again by HPLC. Nuclease resistance was obtained as discussed herein above and the specific method was chosen based on the target and toxicity of the antisense compounds.

Establishment of transgenic mouse pedigrees. The DNA construct used was approximately 600bp (596bp) of the authentic human ACHE promoter followed by the first intron from the AChE gene HpACHE [Ben Aziz-Aloya et al., 1993] to improve its regulation in the transgenic mice, and the AChEcDNA sequence encoding this enzyme. This included the full coding sequence for human AChE [Soreq et al., 1990] and was shown to be expressible in *Xenopus* oocytes and embryos [Ben Aziz Aloya et al., 1993, Seidman et al., 1994]. The transgenic mice were prepared by standard procedures of transformation to obtain transgenic animals, as set forth, for example, in Shani [1985, 1992].

Example 1

To test the idea that overexpressed AChE mediates/modulates neurite growth following brain injury, a rodent model of focal CHI with manifestations resembling head-injured humans [Shohami et al., 1995a; Chen et al., 1996] was employed. Trauma-induced changes in AChE expression and gross dendrite outgrowth in both control and AChE transgenic mice were studied, and these changes were correlated with survival, neurological recovery, and neuronal morbidity. The findings in this Example reveal a prolonged overexpression of AChE following CHI that is accompanied by dramatically enriched dendritic fields in cortex and hippocampus. Moreover, a significantly greater loss of neurons in the hippocampus of AChE transgenic mice correlated with higher morbidity and slow recovery. These data show that distinct short- and long- term management of AChE must be considered in minimizing both acute and delayed dysfunction in head-injured patients.

Materials and Methods

Closed Head Injury: Four-month-old mice were anaesthetized with ether to reach loss of pupillary and corneal reflexes. CHI was performed as described (Chen et al., 1996), all in accordance with the NIH guidelines for the Use and Care of Laboratory Animals and following approval by the Animal Care Committee of the Hebrew University. Severity of the injury was defined by a neurological severity score (NSS) determined 1 hr post-trauma. NSS reflects performance on a battery of 25 parameters established in rats (Shohami et al., 1995a) and adapted to mice (Chen et al. 1996). One score point was accrued for the loss of a tested reflex or the ability to perform tasks requiring varying extents of neuromotor coordination. Recovery was defined as NSS (1 hour) minus NSS at various days following injury and expressed as ΔNSS.

Golgi Impregnation and Image Analysis was Carried out Using De Fano's Cobalt Silver Method Briefly, brains were fixed in 34 mM (1%) cobalt nitrate (18 hours, room temp), impregnated in 117 mM (2w) silver nitrate (24–48 hr, room temp) and processed in fresh Ramon y Cajal's developer. Paraffin sections were toned in 5 mM (0.2%) gold chloride, washed and counterstained with 2 mM alum carmine. Dendritic arborization was assessed by quantifying the Golgi-stained area in pseudo-colored video images using IP labs image analysis software (Signal Analysis Corporation, City, Va.).

Histopathological Examinations were performed 30 days post-injury following transcardial perfusion with 10% phosphate-buffered formalin. Serial coronal sections from fixed brains were paraffin-embedded and stained with hematoxylin-eosin.

In situ hybridization was as described by Andres et al. [1997] and Beeri et al. [1997], using 50-mer 5'-biotinylated 2-O-methyl AChEcRNA probes (Microsynth, Switzerland) and fast-red staining (Boehringer-Mannheim, Germany).

Results

To assess the involvement of AChE towards recovery processes following brain injury, we compared physiological parameters of survival and neurological performance to molecular and cellular measures such as AChEmRNA levels, dendritic growth and neuronal death in AChE-transgenics and control mice.

AChE transaenic mice suffer poor survival and recovery: At the young-adult age of 4 months, ACHE transgenic mice with 2-fold excesses of AChE in their brains were considerably more vulnerable to unilateral closed head injury than sex and age-matched controls. Only 11 out of 14 transgenic, as compared with 9 out of 10 control mice survived the first 24 hrs post-injury. During the following 6 days, another 2 transgenic mice died, leaving 9 out of 14 (65%) (FIG. 1). The 90% survival rate among control FVB/N mice was similar to that displayed by Sabra mice subjected to this same trauma protocol. No further mortality was observed for the duration of the 30 day follow-up period. As overexpression of AChE is expected to reduce the levels of acetylcholine available for mediating cholinergic neurotransmission, the high mortality of AChE transgenic mice following CHI suggests that cholinergic hyperfunction may be critical for survival during an acute phase of recovery lasting from 24 hours up to one week post-trauma.

Persistent post-injury enhancement of AChEmRNA levels: To examine the long-term effect of CHI on AChE production, high resolution in situ hybridization was performed on brain sections from control and transgenic mice before and after head trauma. Prior to injury, a probe detecting both human and murine AChEmRNA transcripts encoding the synaptic (E6) form of AChE confirmed the elevated expression of this message in transgenic mice as compared to controls [Beeri et al. 1997]. Mice were subjected to closed head injury and sacrificed 30 days later. In situ hybridization was performed on 5 $\mu$m brain sections using a biotinylated 2-O-methyl cRNA probe targeted to a consensus domain present in the mRNA encoding synaptic human and mouse AChE [Beeri et al., 1995, 1997]. Staining was with Fast Red.

One month following CHI, in situ hybridization signals appeared considerably enhanced in the contused as compared with contralateral hemispheres of both groups of mice, but were now at least as high in controls as transgenics. Transgenic mice also displayed a larger fraction of dead neurons in this region of hippocampus in both hemispheres. Interestingly, these changes in AChEmRNA levels were particularly apparent in the hippocampus (CA3 region of hippocampus evaluated; see FIG. 2). Transgenic mice also displayed a larger fraction of dead neurons in this region of hippocampus in both hemispheres (FIG. 2). Hybridization with a probe targeted to the alternative "readthrough" AChEmRNA transcript that includes pseudointron $I_4$ revealed no differences either in cortex or in hippocampus of controls and transgenics, both pre- and post-injury (data not shown). These observations demonstrated that the enhanced hybridization signals were attributable exclusively to changes in expression of the AChEmRNA transcript encoding the synapse-targeted enzyme (Sternfeld et al., 1998).

Intensified dendrite growth in the contused transgenic cortex: A wealth of accumulated evidence attributes non-catalytic, neurite-growth-promoting activities to AChE. Dendrite outgrowth is likely an important component in short-term recovery from brain injury [Caceres and Steward, 1983]. To examine the possibility that overexpressed AChE promotes a phase of dendrite outgrowth following CHI, quantitative image analysis was employed of Golgi-stained brain sections from mice prior to and either 4 or 14 days post-trauma. Coronary sections from uninjured (Sham) control and AChE transgenic mice and from mice sacrificed 4 or 14 days post-injury (CHI) were subjected to Golgi staining and to quantitative image analysis. Sham-treated mice underwent the anesthesia and surgical procedure exposing the skull, but were not injured. In all cases, injury was induced over the left hemisphere.

To adapt this approach for use at low magnification facilitating analysis of large populations of neurons, the total Golgi-stained area was quantified in 100–200 $\mu m^2$ fields within cortex and hippocampus. Prior to injury, Golgi staining was 3-fold lower in the parietal cortex of transgenic compared to control mice (Table 1). This was consistent with data obtained previously by tracing dendritic trees of individual neurons at high magnification [Beeri et al., 1997], and was taken to reflect deficient dendritic arborization in cortex of adult transgenic mice.

Table 1 provides a quantitative analysis of total Golgi stained area was performed on coronal brain sections from transgenic (TG) and control (cont) mice prior to (Sham) or either 4 or 14 days post-injury (CHI) as described herein. Two sections from each of n individual mice were included in the analysis. Staining is expressed in arbitrary units and the staining ratio between parallel regions in the injured (left) and uninjured (right) hemispheres was calculated (L/R ratio). Note in the Table the initially low Golgi staining in transgenic as compared to control mice, and the enhanced staining in cortex and hippocampus of the injured side in both groups within 4 days post-trauma (*p=0.02 vs sham-control; **p=0.028 vs sham-TG).

Following head injury, pronounced increases in the Golgi-stained areas were observed in cortex of contused hemispheres, particularly around the site of injury, and especially in transgenic mice. Within 4 days, Golgi-stained areas in the damaged cortex of control mice increased by 38%. In transgenic mice, however, stained areas more than tripled in the parallel cortical region, reaching absolute values similar to those measured in injured control mice. In the contralateral hemispheres, 30% decreased staining in controls and 30% increased staining in transgenics again brought the total absolute staining in cortex to largely similar values between the two groups of mice. These changes were largely stable at least to day 14 post-injury. In the hippocampus, staining increased in both hemispheres of injured control mice, but only in the contused hemisphere of transgenics. Curiously, decreased Golgi staining was observed in the contralateral hippocampus of transgenic mice.

Figure 2A:
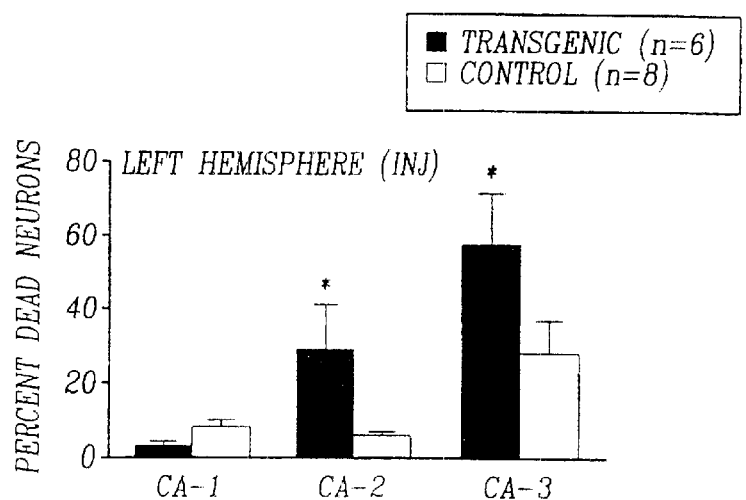
FIGS. 2A–B are graphs showing exaggerated neuron death in hippocampus of AChE transgenic mice following head injury. Five $\mu$m hematoxylin-eosin stained, acidophilic, dead neurons were counted in two consecutive hippocampal sections from brains of control and AChE transgenic mice 30 days following closed head injury. Neuronal loss in the $CA_1$, $CA_2$ and $CA_3$ areas of the hippocampus was expressed as the percentage of dead cells in the total cell population. Graphs represent the percentage of cell loss in the left (A) and right (B) hippocampus of injured mice. Overt neuronal cell death was observed as the appearance of pyknotic black cell bodies. Neurons were counted under the microscope (x40). *$p<0.05$ vs control; **$p<0.01$ vs control.
Figure 2B:
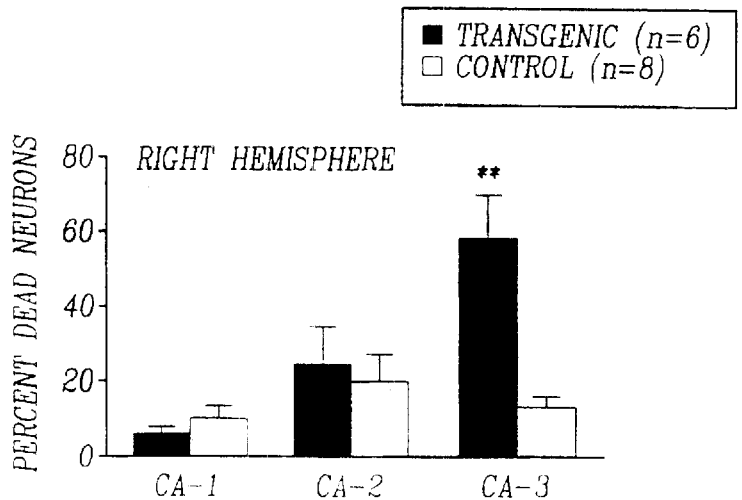

Hippocampal neurons in AChE transqenic mice are prone to trauma-induced cell death: Hippocampal neurons, especially in the CA3 domain, are particularly susceptible to cell death following brain injury [Chen et al., 1996]. One month post-head injury, a limited (<10%) loss of neurons was observed in both CA1 and CA2 of the contused hemisphere in control mice, but pronounced (28%) cell death in CA3 (FIG. 2A). In contrast, transgenic mice displayed 29% and 57% neuron death in CA2 and CA3 of the injured hemisphere, respectively. An even greater difference (55% vs. 15%) between transgenics and controls was observed in the contralateral CA3, but not CA2, region (FIG. 2B). Thus, chronic overexpression of transgenic AChE appears to prime hippocampal neurons in CA3 of both hemispheres for premature death following CHI, and in CA2 only of the contused region.

Figure 3A:
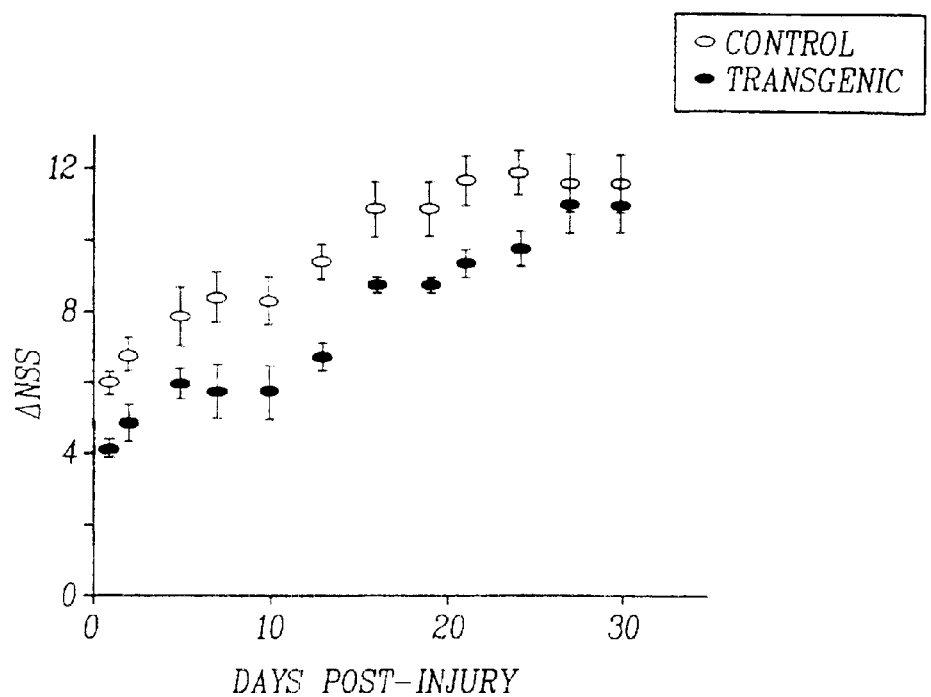
FIGS. 3A–B are graphs showing retarded neurological recovery of AChE transgenic mice following head trauma. Mice were subjected to 25 tests of neurological function 1 hour following closed head injury and assigned a neurological severity score (NSS), as described herein. NSS assessed at the noted days following the injury was compared to that observed at 1 hour and the difference calculated ($\Delta$NSS). Increasing ANSS indicates improved performance and serves as an indicator of recovery (A) Inset represents the fraction of control and transgenic mice able to balance themselves and walk 30 cm along a 2 cm wide beam (B) prior to the injury and at various times following trauma. Note the delayed recovery of neurological functions among AChE transgenic mice throughout the 30 day recovery period. N=10 for both groups of mice.
Figure 3B:
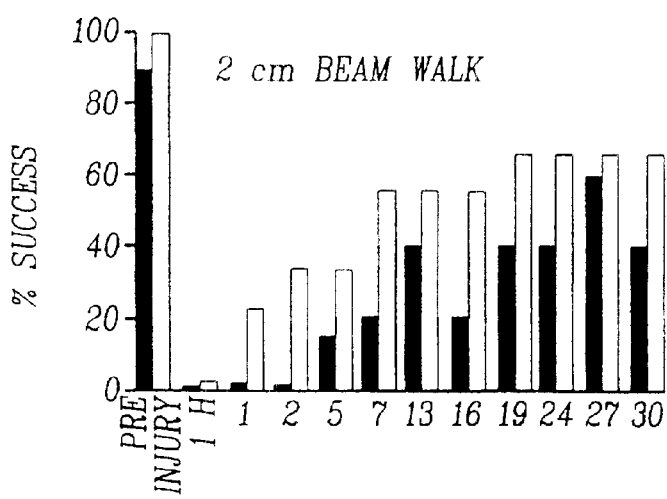

Slow neurological recovery among AChE transgenic mice: In 25 tests of neurological performance that assess various reflexes and neuromotor tasks requiring varying extents of balance and coordinated movement [Chen et al., 1996], non-injured transgenic mice displayed mild impairments (NSS=4.7 vs. 1.3, P<0.05), especially in neuromotor tests such as balancing on a narrow beam [Andres et al., 1997 and FIG. 3B]. One hour post-injury, NSS values reached an average of 16–17 points in both transgenic and control mice, indicating severe trauma. Spontaneous recovery of transgenic survivors lagged behind that of control mice throughout the 30 day follow-up period, especially during the first 10 days (FIG. 3A). Control mice achieved maximal recovery within 19–21 days while transgenic mice required 27–30 days to achieve maximal recovery.

Example 2

Normal and transgenic (Overexpressors of AChE) mice were treated with an AS-ODN (AS3) following closed head injury (CHI) and monitored for survival, behavioral patterns and histopathologic changes with particular reference to the hippocampal neurons. Immediately following CHI both transgenic and nontransgenic mice were treated with AS3, control transgenic and nontransgenic mice with treated with saline. Survival and behavioral responses were monitored for 14 days and then the surviving mice were sacrificed and brains examined for surviving hippocampal neurons.

Hippocampal neurons, especially in the CA3 domain, are particularly susceptible to cell death following brain injury [Shohami et al., 1995, Chen et al., 1996] and AChE trans-genic mice were shown to be exceptionally sensitive to hippocampal cell loss following closed head injury (CHI) in Example 1. Therefore control and AChE transgenic mice were treated with an antisense oligonucleotide directed against AChEmRNA following CHI and measured survival of hippocampal neurons.

Methods

Closed Head Iniury: Four-month-old mice were anesthetized with ether to reach loss of pupillary and corneal reflexes. Closed head injury was performed as described to the left hemisphere [Chen et al., 1996], all in accordance with the NIH guidelines for the Use and Care of Laboratory Animals and following approval by the Animal Care Committee of the Hebrew University. Groups of 10 animals were used, transgenics, non-transgenic FVB/N mice. Immediately following injury, animals were injected with either 50ng 2-O-methyl mouse AS3 antisense oligonucleotide, 5'-CTGCAATATTTTCTTGCACC-3' (SEQ ID No:9) against AChEmRNA or saline directly into the tissue of the site of injury. Fourteen days post-injury, surviving animals were sacrificed and brains were excised and fixed.

Analysis of neuronal death: Acidophilic, dead neurons were counted in two consecutive hippocampal sections (5 Am hematoxylin-eosin stained) 14 days following closed head injury from brains of control or AChE transgenic mice injected with either saline or AS3-ODN. Overt neuronal cell death was observed as the appearance of pyknotic black cell bodies. Neurons were counted under the microscope (×40).

NSS Assessment: was carried out as in Example 1. The ANSS is the summation of 24 distinct neurological tests, similar to the clinically used Glasgo score.

Results

Figure 6A:
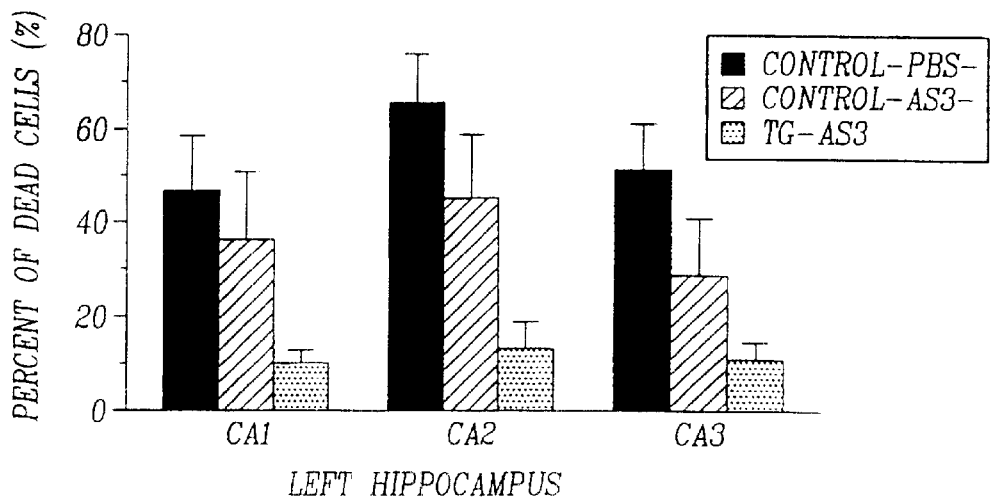
FIGS. 6A–B are bar graphs showing the histological analysis of both control (nontransgenic; cross-hatched bar) and AChE transgenic (stippled bar) mice treated with AS3 as compared with saline (filed bar) of the percentage of cell loss in the left injured (A) and right contralateral (B) hippocampus of traumatized mice.
Figure 6B:
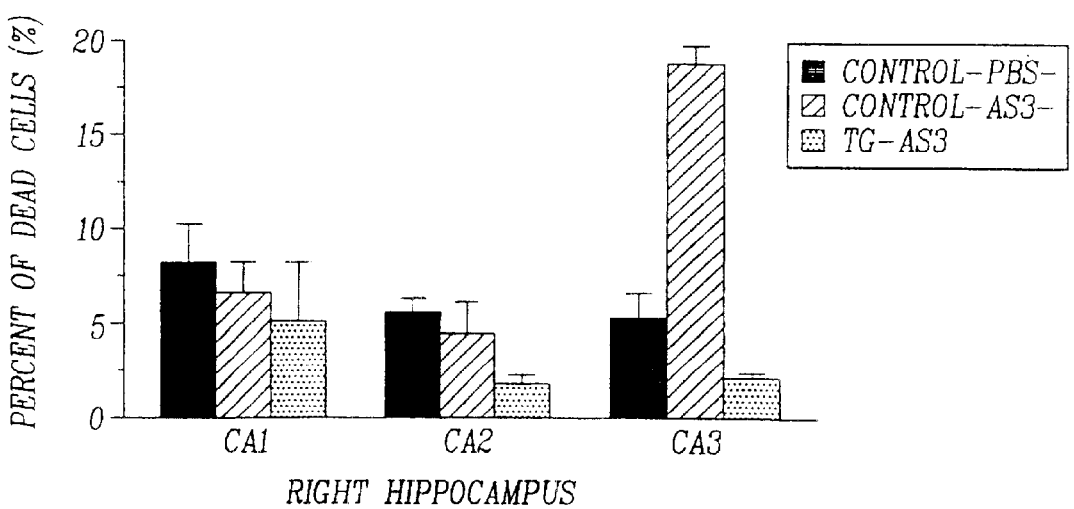

Histological analysis indicated improved survival of hippocampal neuron in both control and AChE transgenic mice treated with AS3 as compared with saline (FIG. 6). Neuronal loss in the CA1, CA2 and CA3 areas of the hippocampus is expressed in the figure as percentage of dead cells in the total relevant cell population. Graphs represent the percentage of cell loss in the left injured (FIG. 6A) and right contralateral (FIG. 6B) hippocampus of traumatized mice. A single administration of AS3 (SEQ ID No:9) oligonucleotide targeted against AChE mRNA protected protect hippocampal neurons following closed head injury in both normal control and AChE transgenic mice.

As shown in Table 2, PBS-injected transgenics suffered drastic mortality (7 out of 10 died at day 5 following injury), when non-transgenic FVB/N mice displayed only 1–2 deaths out of 10 for PBS and AS3 injected animals respectively. Interestingly, only 3 out of the 10 AS3-treated transgenic animals died.

Moreover, the ANSS (recovery score) of PBS-injected transgenics was continuously lower than that of controls, but AS3-treated transgenics performed as well as control mice. Also, as the data shows AS3-treated controls were not harmed by this treatment.

Example 3

As discussed herein above, a strong body of evidence attributes morphogenic activities to the acetylcholine-hydrolyzing enzyme acetylcholinesterase (AChE), especially in association with neurite outgrowth [reviewed by Layer and Willbold, 1995]. An evolutionarily conserved capacity of AChE to promote process extension was observed in avian, amphibian, and mammalian primary neurons [Small et al., 1995; Jones et al., 1995; Sternfeld et al., 1998] and in rat glioma cells [Karpel et al., 1996]. In neuroblastoma cells, modulated expression of AChE revealed a direct correlation between AChE levels and neurite outgrowth [Koenigsberger et al., 1997]. However, the molecular and cellular mechanism(s) by which AChE exerts its neuritogenic activities remain to be elucidated. Repeated observations that process-promoting activities of AChE are insensitive to certain active site inhibitors and to genetically engineered inactivation of its hydrolytic activity demonstrated their non-catalytic nature and indicate a role for AChE in cell adhesion-related processes. Furthermore, they suggested that the neuritogenic function of AChE might be fulfilled, in some circumstances, by catalytically-inactive, AChE-homologous cell surface proteins.

Among the proteins carrying large AChE-like extracellular domains are Drosophila neurotactin [De la Escalera et al., 1990], and gliotactin [Auld et al., 1995], and the rat neuroligins [Ichtchenko et al., 1995]. Unlike AChE, however, the cholinesterase-like proteins all possess a transmembrane region and a protruding cytoplasmic domain. As such, they are capable of transducing growth signals directly into the cell upon extracellular interactions with a protein ligand. In contrast, it is unclear how AChE might induce intracellular signals leading to neurite growth. The possibility was considered that AChE may act by competing with members of the neurotactin/neuroligin family for extracellular binding to common ligands such as neurexins. Neuroligins constitute a multigenic family of brain-specific proteins that have been suggested to exert overlapping functions in mediating recognition processes between neurons [Ichtchenko et al., 1996]. Neuroligins bind to a specific subset of neurexins, polymorphic neuronal cell surface proteins believed to play a role in neuronal differentiation and axogenesis [Ichtchenko et al., 1995; Puschel and Betz, 1995]. Neurexin Iβ was shown to interact with rat neuroligin to induce heterotypic cell adhesion. Thus, neuroligin-neurexin binding interactions could be important in inter-neuronal recognition pathways regulating axon-pathfinding. We previously reported that overexpressed transgenic AChE suppressed neurexin Iβ production in embryonic mouse motoneurons in vivo [Andres et al., 1997]. These results indicate cross-talk between AChE and neurexins during development, and strengthened the concept that AChE and neuroligin act on common elements.

To address the question of whether AChE is obligatory for neurite extension and whether the cholinesterase-like proteins display overlapping functionality, a loss-of-function model was established in which AChE could be replaced by candidate substitutes. In this Example it is shown that stable transfection of rat phaeochromocytoma (PC12) cells with DNA encoding antisense AChE CRNA (AS-ACHE cells) display severe AChE and neurexin 1α mRNA depletion. Following NGF-stimulated differentiation, AS-ACHE cells exhibit an aberrant phenotype characterized by attenuated neuritogenesis. Neuritogenesis was partially restored not only by AChE, but by neuroligin, which also rescued lost neurexin Iα expression.

Materials and Methods

Vector construction: A fragment of rat AChE cDNA was amplified by RT-PCR, using primers designed for the E6 exon of mouse AChE (positions 1728 and 1832). The amplification product was directly cloned into the pCR3 vector (Invitrogen, Leek) according to the manufacturer's instructions. The orientation of the insert was determined by informative restriction analyses using XmnI and PstI (New England Biolabs, Beverly, Mass.) and its nucleotide sequence confirmed in an ABI-377 automated sequencer (Perkin-Elmer, Foster City, Calif.). A pCR3 vector containing an unknown irrelevant DNA fragment served as a control.

Cell lines and transfections: PC12 rat pheochromocytoma cells were grown in Dulbecco modified Eagle medium (DMEM) containing 8% fetal calf serum (FCS) and 8% horse serum (HS) at 37° C., 5% $CO_2$, in a fully humidified chamber. All tissue culture reagents were purchased from Biological Industries (Beth Hahemek, Israel). For the induction of differentiation, 50 ng/ml NGF (Alomone, Jerusalem) was added to the medium with 1% FCS and 1% HS. Tissue culture plates or cover slips were coated with 10 µg/ml collagen type IV (Sigma, St. Louis, Mo.) and for rescue studies also with the same concentration of recombinant human AChE (Sigma). Transient transfections were performed with Lipofectamine™ (GIBCOBRL, Bethesda, USA) according to the manufacturer's instructions. For stable transfections, cells were incubated in medium containing 800 µg/ml G418 (GIBCOBRL) for a period of 30 days and then maintained with 400 µg/ml G418.

Immunocytochemistry: Cells grown on coverslips were methanol fixed for 20 minutes at −20° C. and washed with PBS. Cellular membranes were made permeable by 10 min incubation with PBS containing 0.1% Triton-X100. Non-specific binding was blocked by 1 hour incubation in 3% bovine serum albumin (BSA). Two µg/ml polyclonal anti-AChE antiserum (gratefully received from I. Silman) was added for 1 hour at room temperature, followed by a Texas red-conjugated anti-rabbit antibody (Molecular Probes, Leiden). Images were digitized using a Cohu 4915 charge coupled device (CCD) camera coupled to a Zeiss Axioplan microscope.

Morphological measurements: PC12 or AS-ACHE cells subjected for 3 days to NGF differentiation were stained using May-Grunwald stain (Sigma) followed by Gurr's improved Giemsa stain (BDH). Images of differentiating cells were captured using a CCD camera. Neurite numbers per cell were manually counted and cell body measurements were quantified using the program IpLab Spectrum (Signal Analytics, Vienna, Va., USA).

Results

Antisense suppression elicits differentiation-resistant chances in AChE production and assembly.

To achieve potent long-term suppression of AChE production, the pCRAS-E6 vector was constructed, expressing a 132 bp fragment of exon 6 from the rat ACHE gene in the antisense orientation under the control of the proximal promoter-enhancer region of cytomegalovirus. A neomycin resistance gene included in the vector, allowed for the isolation of stable PC12 transfectants expressing the antisense AChE cRNA. Eight independent clones were selected, each displaying different expression levels of AChE cRNA. One of these clones, termed AS-ACHE was employed for further analyses.

AChE mRNA levels were measured in PC12 and AS-ACHE cells by kinetic follow-up of RT-PCR reaction products. Specific primers selective for exon 6 (E6) or pseudointron 4 (I4) revealed a 10-fold reduction in AChE-E6 mRNA and complete suppression of the "readthrough" AChE-I4 mRNA transcripts. This indicated an antisense-induced destruction of nascent, unprocessed nuclear AChE mRNA transcripts.

AChE catalytic activity was suppressed by 80% in AS-ACHE cells as compared to the original PC12 cell line. It was not significantly enhanced by NGF-triggered differentiation, in contrast to the 50% increase observed in the original PC12 cells within 24 hours of NGF treatment [Grifman and Soreq, 1997]. The ratio of AChE monomers and dimers to tetramers was 2-fold higher in naive AS-ACHE cells as compared to the original PC12 cell line. NGF treatment, which increased this ratio in PC12 cells, did not significantly affect this ratio in AS-ACHE cells.

AChE suppression is associated with a partially reversible neuritogenic deficit.

Figure 7:
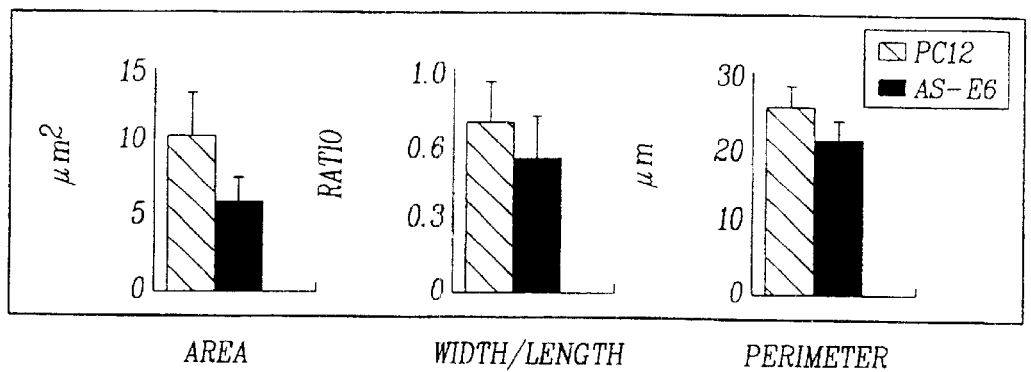
FIG. 7 are bar graphs showing Morphometric cell body changes due to AChE suppression is associated with a rescuable neuritogenic deficiency wherein PC12 (hatched columns) and AS-ACHE cells (filled columns) grown in the presence of NGF for 48 hours were stained with May-Grunwald and Giemsa and subjected to measurement of cell body areas, perimeters and width/length ratios as detailed under Materials and Methods. Shown are values and standard deviations derived from 100 cells in 3 cultures, $p<0.01$, (2-tailed t-test).
Figure 8A:
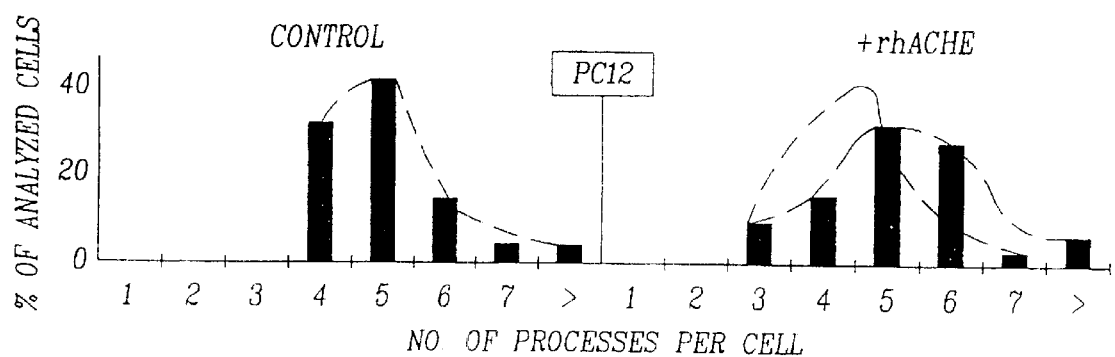
FIGS. 8A and B are graphs showing Reversibility of the neuritogenic deficiency wherein PC12 (upper panel), FIG. 8A and AS-ACHE cells (lower panel), FIG. 8B grown for 48 hours in the presence of NGF were stained with May-Grunwald and Giemsa and process Number per cell counted. Depicted are percent values of analyzed cells with various process Nos. before (control) or after growth on a matrix including 10 $\mu$g/ml recombinant human AChE (+rhAChE) Note the rightward shift in each cell population under rhAChE treatment. While the difference in the distribution of neurite frequencies (shown in hatched line for each cell population) was not significant for PC12 cells, it was significant ($p<0.01$) in AS-ACHE cells. N=50 cells for each population.
Figure 8B:
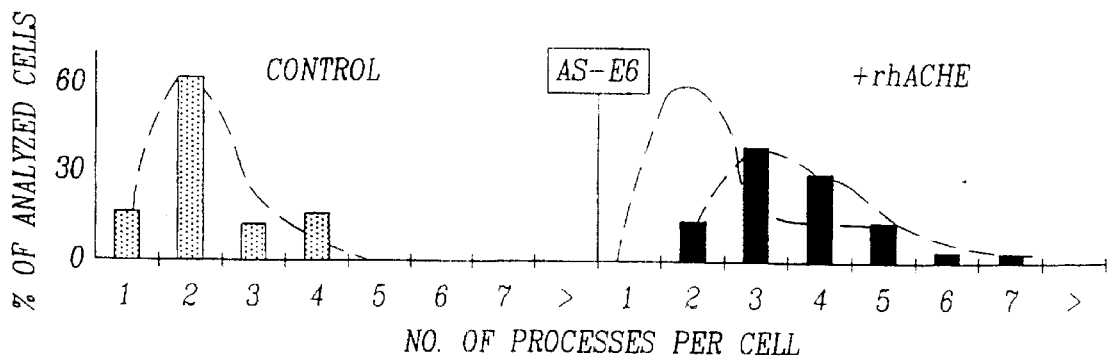
Figure 9A:
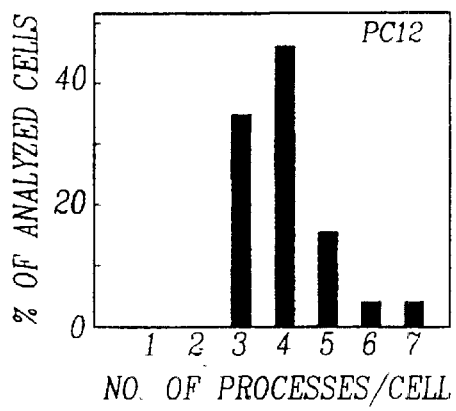
FIGS. 9A–F are graphs showing the redundancy of AChE variants and neuroligin-1 in restoring the deficient neuritogenic capacity of AS-ACHE cells. The process number per cell is presented as percent of analyzed cells in each population (N=50 cells in each case). Note "rescue" of neuritogenesis from AS-ACHE cells by transfection with either active or inactive AChE variants and neuroligin, but not the StAR control.
Figure 9B:
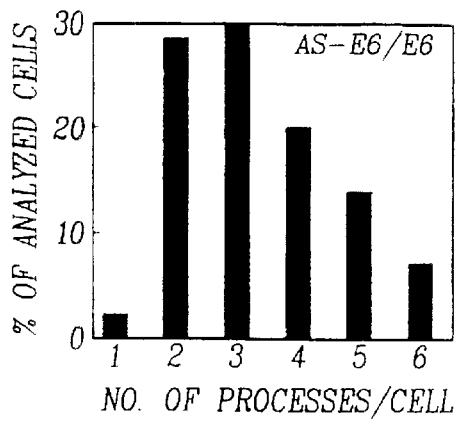
Figure 9C:
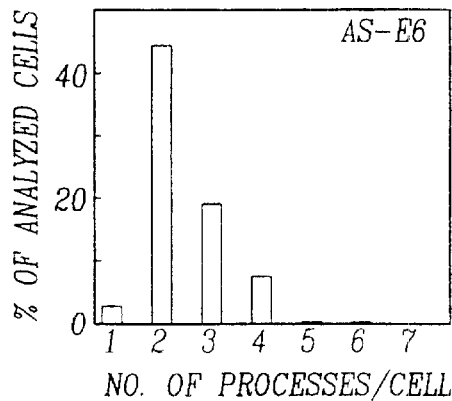
Figure 9D:
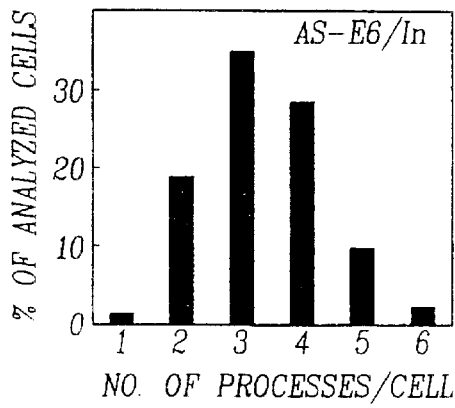
Figure 9E:
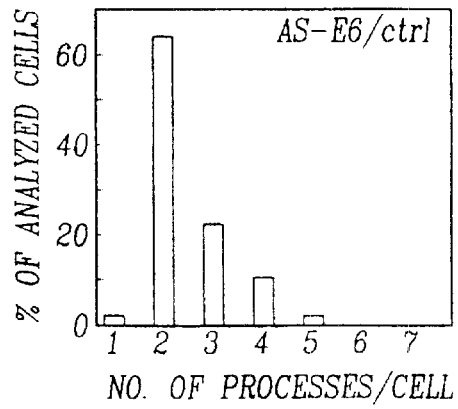
Figure 9F:
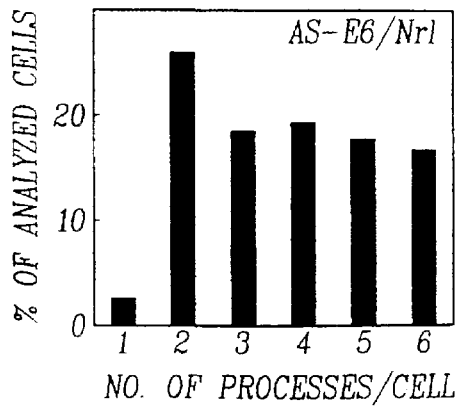

Immunofluorescence detection using a polyclonal antibody specific for rodent AChE revealed a conspicuous reduction in AChE protein in differentiated AS-ACHE as compared to PC12 cells, extending the biochemical measurements. Immunofluorescent staining of neurofilament 200 and NCAM revealed identical levels of these proteins in PC12 and AS-ACHE cells, demonstrating the selectivity of this suppression and the preserved neuronal identity of the AS-ACHE cells. However, antisense suppression of AChE reduced cell body areas, perimeters and width/length ratios of AS-ACHE as compared to the original PC12 cells (FIG. 7). Moreover, it significantly reduced neurite frequency following NGF treatment from the 5.0±1.0 neurites/cell (avg±s.d) displayed by PC12 cells to 2.2±0.9 neurites/cell ($p<0.01$, 2 tailed t-test) in AS-ACHE cells (FIG. 8). To examine the reversibility of this antisense ACHE-induced phenotype, the collagen matrix on which the cells were grown was coated with highly purified recombinant human AChE (rhAChE). Following 3 days in the presence of NGF, neurite frequency increased significantly ($p<0.01$) to 3.5±1.1 neurites/cell among AS-ACHE cells plated on the rhAChE-containing matrix (FIG. 8). In contrast, neurite frequencies remained essentially similar in the original PC12 cells grown with or without rhAChE (5.2±1.2 as compared to 5.0±1.0). Rescue of the AChE-deficient neuritogenic phenotype by matrix-bound extracellular AChE suggests that interactions taking place on the surface of the cells determine, at least in part, the neuritogenic capacity of PC12 cells.

Both AChE and neuroligin rescue neuritogenesis in AS-ACHE cells.

The reversibility of the AS-ACHE phenotype made these cells an appropriate model system to test whether AChE is obligatory for neuritogenesis and if other proteins are also able to restore neuritogenesis. The deficient neurite outgrowth observed in AS-ACHE cells could be related to lost catalytic activities of AChE, non-catalytic structural properties or both. To test each of these possibilities, we transiently transfected AS-ACHE cells with plasmids encoding the synaptic form of AChE [AChE-E6, Seidman et al., 1995], genetically inactivated AChE [AChE-In, Sternfeld et al., 1998], the catalytically-inactive AChE homolog neuroligin-1 [Ichtchenko et al., 1995] or a plasmid coding for the mitochondrial protein StAR [Clark et al., 1994] as a control.

The initial neurite frequency of AS-ACHE cells was 1.9±0.7 neurites/cell in these experiments, and remained low (2.4±0.1 neurites/cell) following transient transfections with the irrelevant StAR plasmid. However, transfection with AChE-E6, AChE-E6-In and neuroligin-1 enhanced neurite frequency to 3.3±0.1, 3.3±0.1 and 3.7±0.5 neurites/cell, respectively, with similar statistical significance ($p<0.01$, FIG. 9). By rescuing neurite outgrowth with AChE-E6-In, these data confirmed the non-catalytic nature of AChE's neuritogenic activity in PC12. Moreover, they demonstrated an overlapping functionality of AChE and neuroligin in promoting neuritogenesis in these cells.

Discussion

In this Example the neuritogenic activities of AChE using a reversible AChE loss-of-function model in PC12 cells expressing antisense AChE cRNA were studied. Stable suppression of AChE in PC12 cells imposed a block to normal NGF-mediated differentiation that was characterized by altered cytoarchitecture, a paucity of neurites, and loss of neurexin Iα mRNA. These findings that heterologous expression of neuroligin-1 rescued both morphological characteristics and gene expression patterns associated with normal differentiation demonstrate a functional redundancy of AChE and neuroligin in stimulating a critical morphogenetic pathway in these cells. Together with the sequence homologies shared by AChE, neuroligins, neurotactin and gliotactin, these data suggest that AChE and the various cholinesterase-like proteins bind an overlapping set of heterotypic ligands such as neurexins and neurexin-like proteins.

Rather than complete functional redundancy in vivo, these experiments most likely reflect unique yet related roles for AChE and neuroligin in neuritogenesis. It was previously shown that the core domain of AChE could replace the homologous extracellular domain of neurotactin to generate a functional chimera [Darboux et al., 1996]. Thus, the cholinesterasic domain appears to play a conserved role in ligand recognition. Nevertheless, a membrane-associated form of the intact AChE polypeptide could not substitute for neurotactin in mediating heterotypic cell adhesion. Thus, the transmembrane and cytoplasmic elements present in the AChE-like proteins—but absent in AChE—appear indispensable in translating ligand binding to changes in cytoarchitecture. In that case, competitive binding of AChE to neurexins could serve a unique role in regulating growth processes associated with neuroligin-neurexin interactions.

As these cells were grown at low density on a collagen matrix, the observations in PC12 must reflect autologous interactions between AChE, neuroligin, and a common ligand, most likely neurexin Iα. Other in vitro models in which neurite-promoting activities for AChE were demonstrated also reflect autologous activities in cell cultures. These studies therefore imply that lateral cis membrane interactions between AChE, neuroligin, and neurexin can mediate neuritogenic processes in a variety of neuronal cell types. However, these in vitro studies do not exclude in vivo situations in which heterotypic trans cell-cell interactions could predominate. Both AChE and neurexins are expressed in the developing nervous system and are considered to play central roles in establishing neuronal connectivity. Yet, the rescuable nature of the AS-ACHE phenotype demonstrates a previously unrecognized plasticity in AChE-mediated morphogenetic processes and therefore provide a role for non-catalytic activities of AChE in neuronal remodeling in the adult nervous system. Thus, the reduced AChE levels observed in the adrenal gland of Alzheimer's disease patients [Appleyard and McDonald, 1991] predict modified innervation of the adrenal medulla. Consistent with this, we have recently observed high expression of AChE to be associated with modulated dendrite branching in AChE transgenic mice [Beeri et al., 1997] and in mice subjected to closed head injury (Examples 1, 2).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Golgi staining in cortex and hippocampus before and after closed head injury.

| group | n | Cortex Left (Inj) | Cortex Right | L/R ratio (cortex) | Hippocampus Left (Inj) | Hippocampus Right | L/R ratio (hipp) |
|---|---|---|---|---|---|---|---|
| Sham-cont | 6 | 2.34 ± 0.35 | 2.41 ± 0.41 | 0.97 | 0.79 ± 0.28 | 0.85 ± 0.35 | 0.93 |
| Sham-TG | 2 | 0.81 ± 0.36* | 0.77 ± 0.27* | 1.07 | 0.80 ± 0.19 | 0.75 ± 0.19 | 1.07 |
| CHI-cont 4d | 3 | 3.23 ± 0.19 | 1.47 ± 0.1 | 2.19 | 2.22 ± 0.16 | 1.31 ± 0.21 | 1.69 |
| CHI-TG 4d | 3 | 3.07 ± 0.43 | 1.40 ± 0.15 | 2.19 | 1.44 ± 0.16 | 0.75 ± 0.07 | 1.92 |
| CHI-cont 14d | 10 | 3.18 ± 0.43 | 1.58 ± 0.29 | 2.01 | 1.27 ± 0.10 | 1.08 ± 0.15 | 1.17 |
| CHI-TG 14d | 4 | 3.01 ± 0.67** | 1.21 ± 0.32 | 2.48 | 1.31 ± 0.18 | 0.52 ± 0.12 | 2.52 |

NSS Assessment for AchE Transgenic Mice Following CHI

| Group Date: 21/1/98 | Mouse No. | Neurological Severity Score 1 h | 24 h | 48 h | 5 days | 7 days | 10 days | d-NSS 24 h | 48 h | 5 days | 7 days | 10 days |
|---|---|---|---|---|---|---|---|---|---|---|---|---|
| Control-PBS | 1 | 17 | 11 | 11 | 10 | 9 | 9 | 6 | 6 | 7 | 8 | 8 |
| Mortality: | 2 | 19 | | | | | | | | | | |
| 24 h: 1/9 | 3 | 16 | 12 | 11 | 10 | 9 | 9 | 4 | 5 | 6 | 7 | 7 |
| | 4 | 18 | 14 | 11 | 10 | 10 | 10 | 4 | 7 | 8 | 8 | 8 |
| | 5 | 15 | 11 | 11 | 9 | 8 | 8 | 4 | 4 | 6 | 7 | 7 |
| | 6 | 17 | 12 | 11 | 9 | 9 | 9 | 5 | 6 | 8 | 8 | 8 |
| | 7 | 18 | 12 | 12 | 10 | 9 | 9 | 6 | 6 | 8 | 9 | 9 |
| | 8 | 18 | 14 | 13 | 12 | 11 | 10 | 4 | 5 | 6 | 7 | 8 |
| | 9 | 19 | 13 | 12 | 10 | 10 | 10 | 6 | 7 | 9 | 9 | 9 |
| | N | 9 | 8 | 8 | 8 | 8 | 8 | 8 | 8 | 8 | 8 | 8 |
| | Average | 17.44 | 12.38 | 11.50 | 10.00 | 9.38 | 9.25 | 4.88 | 5.75 | 7.25 | 7.88 | 8.00 |
| | SD | 1.33 | 1.19 | 0.76 | 0.93 | 0.92 | 0.71 | 0.99 | 1.04 | 1.16 | 0.83 | 0.76 |
| | SEM | 0.44 | 0.42 | 0.27 | 0.33 | 0.32 | 0.25 | 0.35 | 0.37 | 0.41 | 0.30 | 0.27 |
| Control-AS3 | 1 | 18 | 14 | 14 | 12 | 11 | 11 | 4 | 4 | 6 | 7 | 7 |
| (1 ng/ul) | 2 | 17 | 11 | 11 | 9 | 8 | 8 | 6 | 6 | 8 | 9 | 9 |
| Mortality: | 3 | 16 | 11 | 11 | 10 | 10 | 9 | 5 | 5 | 6 | 6 | 7 |
| 1 h: 1/10 | 4 | 16 | 11 | 11 | 9 | 9 | 8 | 5 | 5 | 7 | 7 | 8 |
| 24 h: 1/9 | 5 | 18 | 14 | 14 | 14 | | | 4 | 4 | 4 | | |
| | 6 | 19 | | | | | | | | | | |
| | 7 | 19 | 14 | 13 | 11 | 11 | 11 | 5 | 6 | 8 | 8 | 8 |
| | 8 | | | | | | | | | | | y |
| | 9 | 16 | 12 | 12 | 10 | 10 | 10 | 4 | 4 | 6 | 6 | 6 |
| | 10 | 17 | 12 | 11 | 11 | 10 | 9 | 5 | 6 | 6 | 7 | 8 |
| | N | 9 | 8 | 8 | 8 | 7 | 7 | 8 | 8 | 8 | 7 | 7 |
| | Average | 17.33 | 12.38 | 12.13 | 10.75 | 9.86 | 9.43 | 4.75 | 5.00 | 6.38 | 7.14 | 7.57 |
| | SD | 1.22 | 1.41 | 1.36 | 1.67 | 1.07 | 1.27 | 0.71 | 0.93 | 1.30 | 1.07 | 0.98 |
| | SEM | 0.41 | 0.50 | 0.48 | 0.59 | 0.40 | 0.48 | 0.25 | 0.33 | 0.46 | 0.40 | 0.37 |
| TG-PBS | 1 | 19 | 14 | 12 | 12 | 11 | 10 | 5 | 7 | 7 | 8 | 9 |
| Mortality: | 2 | 14 | 10 | 10 | 10 | 10 | 10 | 4 | 4 | 4 | 4 | 4 |
| 1 h: 3/10 | 3 | 19 | | | | | | | | | | |
| 24 h: 3/7 | 4 | 19 | | | | | | | | | | |
| 5 d: 1/4 | 5 | 19 | 15 | 15 | | | | 4 | 4 | | | |
| | 6 | 19 | | | | | | | | | | |
| | 7 | 20 | 16 | 15 | 14 | 13 | 12 | 4 | 5 | 6 | 7 | 8 |
| | 8 | | | | | | | | | | | |
| | 9 | | | | | | | | | | | |
| | 10 | | | | | | | | | | | |
| | N | 7 | 4 | 4 | 3 | 3 | 3 | 4 | 4 | 3 | 3 | 3 |
| | Average | 18.43 | 13.75 | 13.00 | 12.00 | 11.33 | 10.67 | 4.25 | 5.00 | 5.67 | 6.33 | 7.00 |
| | SD | 1.99 | 2.63 | 2.45 | 2.00 | 1.53 | 1.15 | 0.50 | 1.41 | 1.53 | 2.08 | 2.65 |
| | SEM | 0.75 | 1.31 | 1.22 | 1.15 | 0.88 | 0.67 | 0.25 | 0.71 | 0.88 | 1.20 | 1.53 |
| TGI-AS3 | 1 | 18 | 14 | 11 | 9 | 9 | 9 | 4 | 7 | 9 | 9 | 9 |
| (1 ng/ul) | 2 | 14 | 9 | 9 | 7 | 7 | 7 | 5 | 5 | 7 | 7 | 7 |
| Mortality: | 3 | 17 | 12 | 11 | 9 | 9 | 8 | 5 | 6 | 8 | 8 | 9 |
| 1 h: 1/9 | 4 | 19 | | | | | | | | | | |
| 24 h: 2/8 | 5 | 18 | 13 | 13 | 10 | 9 | 9 | 5 | 5 | 8 | 9 | 9 |
| | 6 | 15 | 9 | 9 | 8 | 8 | 8 | 6 | 6 | 7 | 7 | 7 |
| | 7 | 19 | | | | | | | | | | |
| | 8 | 19 | 15 | 15 | 14 | 13 | 12 | 4 | 4 | 5 | 6 | 7 |
| | 9 | | | | | | | | | | | |
| | N | 8 | 6 | 6 | 6 | 6 | 6 | 6 | 6 | 6 | 6 | 6 |

-continued

NSS Assessment for AchE Transgenic Mice Following CHI

| Group Date: | Mouse | Neurological Severity Score | | | | | | d-NSS | | | | |
|---|---|---|---|---|---|---|---|---|---|---|---|---|
| | | 1 h | 24 h | 48 h | 5 days | 7 days | 10 days | 24 h | 48 h | 5 days | 7 days | 10 days |
| 21/1/98 | No. | | | | | | | | | | | |
| | Average | 17.38 | 12.00 | 11.33 | 9.50 | 9.17 | 8.83 | 4.83 | 5.50 | 7.33 | 7.67 | 8.00 |
| | SD | 1.92 | 2.53 | 2.34 | 2.43 | 2.04 | 1.72 | 0.75 | 1.06 | 1.37 | 1.21 | 1.10 |
| | SEM | 0.68 | 1.03 | 0.95 | 0.98 | 0.83 | 0.70 | 0.31 | 0.43 | 0.56 | 0.49 | 0.45 |

REFERENCES

Agarwal et al., 1991. Proc. Natl. Acad. Sci. USA, 88:7595.

Agrawal, 1996. Antisense oligonucleotides: towards clinical trials, TIBTECH, 14:376.

Andres, et al. (1997). Acetylcholinesterase-transgenic mice display embryonic modulations in spinal cord choline acetyltransferase and neurexin I beta gene expression followed by late-onset neuromotor deterioration. Proc. Natl. Acad. Sci. USA, 94:8173–8.

Appleyard and McDonald (1991). Reduced adrenal gland acetylcholinesterase activity in Alzheimer's disease. Lancet, 338:1085–1086.

Arendt, et al (1995). Dendritic reorganisation in the basal forebrain under degenerative conditions and its defects in Alzheimer's disease. II. Ageing, Korsakoff's disease, Parkinson's disease, and Alzheimer's disease. J. Comp. Neurol. 351:169–88.

Auld, et al. (1995). Gliotactin, a novel transmembrane protein on peripheral glia, is required to form the blood-nerve barrier in Drosophila. Cell 81:757–767.

Beeri, et al (1995). Transgenic expression of human acetylcholinesterase induces progressive cognitive deterioration in mice. Current Biology 5:1063–1071.

Beeri et al (1997). Enhanced hemicholinium binding and attenuated dendrite branching in cognitive impaired AChE-transgenic mice. J. Neurochem 69:2441–51.

Ben-Aziz et al. (1993). Promoter elements and alternative splicing in the human ACHE gene. Prog. Brain Res. 98:147–53.

Ben Aziz-Aloya et al. (1993) "Expression of a human acetylcholinesterase promoter-reporter construct in developing neuromuscular junctions of Xenopus embryos" Proc. Natl. Acad. Sci. USA, 90:2471–2475.

Betz et al., 1994, Basic Neurochem. Molecular Cell, (Raven Press Ltd, N.Y.) 5th Ed., 681–699.

Boado and Pardridge, 1992. Complete protection of antisense oligonucleotides against serum nuclease degradation by an avidin-biotin system. Bioconjug. Chem. 3, 519–523.

Bickel, et al., 1993, "Pharmacologic effects in vivo in brain by vector-mediated peptide drug delivery" Proc. Natl. Acad. Sci. USA 90(7)2618–2622.

Bjorklund and Stenevi, "Intracerebral neural grafting: a historical perspective" in Bjorklund, A. and U. Stenevi, eds. Neural grafting in the mammalian CNS, Amsterdam: Elsevier, 3–11 (1985).

Bjorklund, "Dopaminergic transplants in experimental Parkinsonism: Cellular mechanisms of graft-induced functional recovery" Current Biology, 2:683–689 (1992).

Brem et al., "Polymers as controlled drug delivery devised for the treatment of malignant brain tumors" Eur. J. Pharm. Biopharm 39:2–7 (1993).

Buell and Coleman (1979). Dendritic growth in the aged human brain and failure of growth in senile dementia. Science 206:854–6.

Caceres and Steward (1983). Dendritic reorganization in the denervated gyrus of the rat following entorhinal cortical lesions: A golgi and electron microscopic analysis. J. Comp. Neurol. 214:387–403.

Calabretta, et al, 1996. Antisense strategies in the treatment of leukemias, Semin. Oncol. 23:78.

Caprusi and Levine, 1992. Cognitive impairment following closed head injury. Neurologic. Clin., 10:879–893.

Chen et al. (1996). An experimental model of closed head injury in mice: Pathophysiology, histopathology and cognitive deficits. J. Neurotrauma 13:557–568.

Chen et al. (1997A). Cerebroprotective effects of ENA-713, a novel acetylcholinesterase inhibitor, in closed head injury in the rat. Brain Res. in press.

Chen et al (1997b). Motor and cognitive deficits in Apolipoprotein E-deficient mice after closed head injury. Neuroscience, 80:1255–1262.

Clark, et al. (1994). The purification, cloning, and expression of a novel luteinizing hormone-induced mitochondrial protein in MA-10 mouse Leydig tumor cells. Characterization of the steroidogenic acute regulatory protein (StAR). J Biol Chem, 269:28314–28322.

Crooke, 1995. Progress in antisense therapeutics, Hematol. Pathol. 2:59.

Darboux, et al. (1996). The structure-function relationships in Drosophila neurotactin shows that cholinesterasic domains may have adhesive properties. EMBO J. 15:4835–4843.

De la Escalera, et al. (1990). Characterization and gene cloning of neurotactin, a Drosophila transmembrane protein related to cholinesterases. EMBO J, 9:3593–601.

Dixon, et al (1994). Increased anticholinergic sensitivity following closed skull impact and controlled cortical impact traumatic brain injury in the rat. J. Neurotrauma 11:275–287.

Eckstein 1985. Ann. Rev. Biochem. 54:367–402.

Flood and Coleman (1990). Hippocampal plasticity in normal aging and decreased plasticity in Alzheimer's disease. Prog. Brain Res. 83:435–43.

French et al. (1991). A case-control study of dementia of the Alzheimer type. Am. J. Epidemiol. 121:414–421.

Friedman, et al (1996). Pyridostigmine brain penetration under stress enhances neuronal excitability and induces early immediate transcriptional response. Nature Medicine 2:1382:1385.

Gennarelli, (1997). The pathobiology of traumatic brain injury. Neuroscientist 3:73–81.

Gentleman et al. 1993). Molecular pathology of head trauma: Altered βAPP metabolism and the aetiology of Alzheimer's disease. Prog. Brain Res. 96:237–246.

Gordon, et al (1995). Memory deficits and cholinergic impairments in apolipoprotein E- deficient mice. Neurosci. Lett. 199:1–4.

Gorman, et al (1989). Analysis of acetylcholine release following concussive brain injury in the rat. J. Neurotrauma 6:203.

Grifman and Soreq, (1997). Differentiation intensifies the susceptibility of phaeochromocytoma cells to antisense oligodeoxynucleotide-dependent suppression of acetylcholinesterase activity. Antisense Research and Nucleic Acids Drug Development 7:351–359.

Grifman et al., 1997. Potential antisense oligonucleotide therapies for neurodegenerative diseases. In *Concepts in Gene Therapy*, M. Strauss and J. A. Barranger, eds. (Walter de Gruyter & Co., Berlin)

Hamm et al., (1993). Cognitive impairment following traumatic brain injury: the effect of pre-and post-injury administration of scopolamine and MK-801. Cognitive Brain Res. 1:223–226.

Hamm et al. (1996). Working memory deficits following traumatic brain injury in the rat. J. Neurotrauma 13:317–323.

Hampel and Tritz, 1989. RNA Catalytic Properties of the Minimum (−) sTRSV Sequence. Biochemistry 28:4929–4933.

Ichtchenko, et al. (1995). Neuroligin 1: a splice site-specific ligand for α-neurexins. Cell 81:435–443.

Isacson et al., "Graft-induced behavioral recovery in an animal model of Huntington's disease" Proc. Natl. Acad. Sci., 83:2728–2732 (1986).

Iyer et al. 1990. *J. Org. Chem.*, 55:4693–4699.

Jones, et al. (1995). The effect of acetylcholinesterase on outgrowth of dopaminergic neurons in organotypic slice culture of rat midbrain. Cell Tissue Res. 279:323–330.

Karpel, et al. (1996). Overexpression of alternative human acetylcholinesterase forms modulates process extensions in cultured glioma cells. J. Neurochem. 66:114–123.

Koenigsberger et al. (1997). Neurite differentiation is modulated in neuroblastoma cells engineered for altered acetylcholinesterase expression. J. Neurochem. 69:1389–97.

Layer and Willbold (1995). Novel functions of cholinesterases in development, physiology, and disease. Prog. Histochem. Cytochem. 29:1–94.

Lehmann, et al (1997). Synergy between the genes for butyrylcholinesterase k variant and apolipoprotein e4 in late onset confirmed Alzheimer's Disease. Hum. Molec. Genet. 6:1933–1936.

Lefebvre-d'Hellencourt, et al, 1995. Immunomodulation by cytokine antisense oligonucleotides, Eur. Cytokine Netw., 6:7.

Lev-Lehman et al., 1997. Antisense Oligomers in vitro and in vivo. In *Antisense Therapeutics*, A. Cohen and S. Smicek, eds (Plenum Press, New York)

Lillie (1965). Histopathologic Technic and Practical Histochemistry, Third edition. The Balkiston Division McGraw-Hill Book Co. New York, Toronto, Sydney, London, pp. 290–291.

Lindvall et al., "Transplantation in Parkinson's disease: two cases of adrenal medullary grafts to the putamen" Ann. Neurol., 22:457–468 (1987).

Lindvall et al., "Grafts of fetal dopamine neurons survive and improve motor function in Parkinson's disease" Science, 247:574–577 (1990).

Loewenstein-Lichtenstein, et al (1995). Genetic predisposition to adverse consequences of anti-cholinesterases in 'atypical' BCHE carriers. Nat. Med. 1:1082–5.

Martinez-Pastor, M. T., Marchler, G., Schuller, C., Marchler Bauer, A., Ruis, H., and Estruch, F. (1996). The Saccharomyces cerevisiae zinc finger proteins Msn2p and Msn4p are required for transcriptional induction through the stress response element (STRE). EMBO J. 15:2227–35.

Mayeux et al., 1995. Synergistic effects of traumatic head injury and apolipoprotein-ε4 in patients with Alzheimer's disease. Neurology, 45:555–557.

Morrison, J. 1991. *J. Biol. Chem.*, 266:728.

Pardridge, et al., 1992, "Blood-brain barrier and new approaches to brain drug delivery" West J. Med. 156(3) 281–286.

Pardridge, 1992, "Recent Developments in peptide drug delivery to the brain" Pharm. Toxicol. 71(1):3–10.

Purves and Hadley (1985). Changes in the dendritic branching of adult mammalian neurones revealed by repeated imaging in situ. Nature 315:404–6.

Puschel and Betz (1995). Neurexins are differentially expressed in the embryonic nervous system of mice. J Neurosci. 15:2849–2856.

Rosolen et al., 1990. *Cancer Res.*, 50:6316.

Sanberg et al., "Cell transplantation for Huntington's disease" R. G. Landes Co., Boca Raton, Fla., pp. 19–21 (1994).

Seidman et al. (1994) "Overexpressed monomeric human acetylcholinesterase induces subtle ultrastructural modifications in developing neuromuscular junctions of Xenopus laevis embryos" *J. Neurochem.* 62:1670–1681.

Seidman, et al. (1995). Synaptic and epidermal accumulations of human acetylcholinesterase are encoded by alternative 3'-terminal exons. Mol. Cell. Biol. 15:2993–3002.

Shani (1985) "Tissue specific expression of rat myosin light chain 3 gene in transgenic mice" Nature 314:283–286.

Shani et al. (1992) "Expression of human serum albumin in the milk of transgenic mice" Transgen. Res. 1:192–208.

Shohami et al (1995a). Long-term effect of HU-211, a novel non-competitive NMDA antagonist, on motor and memory functions after closed head injury in the rat. Brain Res. 674:55–62.

Shohami et al (1995b). The effect of the adrenocortical axis upon recovery from closed head injury. J. Neurotrauma. 12:1069–1077.

Shohami et al (1997). Oxidative Stress in Closed Head Injury: brain antioxidant capacity as an indicator of functional outcome. J. Cereb. Blood Flow & Metabol. 17:1007–1019.

Siesjo (1993). Basic mechanisms of traumatic brain damage. Ann. Emerg. Med. 22:959–969.

Sarver et al., 1990, Gene Regulation and Aids, pp. 305–325.

Shaw et al., 1991. *Nucleic Acids Res.*, 19:747–750.

Small, et al. (1995). Cholinergic regulation of neurite outgrowth from isolated chick sympathetic neurons in culture. J. Neurosci. 15, 144–151.

Spitzer and Eckstein 1988. Inhibition of deoxynucleases by phosphorothioate groups in oligodeoxyribonucleotides. Nucleic Acids Res. 18:11691–11704.

Symons (1989) "Self-cleavage of RNA in the replication of small pathogens of plants and animals", *TIBS* 14:445–450.

Symons (1992) "Small Catalytic RNAs", *Annu. Rev. Biochem.* 61:641–671.

Sullivan (1994) "Development of Ribozymes for Gene Therapy", *J. Investigative Dermatology* (Suppl) 103:95S.

Soreq, et al., 1990. Molecular cloning and construction of the coding region for human acetylcholinesterase reveals a G+C-rich attenuating structure, Proc. Natl. Acad. Sci. USA, 87:9688–9692.

Sternfield, et al (1998). Acetylcholinesterase enhances neurite growth and synapse development through alternate contributions of its hydrolytic capacity, core protein and variable C-termini. J. Neurosci. In press.

Uhlenbeck, 1987. "Small catalytic oligoribonucleotide" Nature 328:596–600.

Velan et al. (1991a) "Recombinant human acetylcholinesterase is secreted from transiently transfected 293 cells as a soluble globular enzyme," Cell. Mol. Neurobiol. 11:143–156.

Velan et al. (1991b) "The effect of elimination of inter-subunit disulfide bonds on the activity, assembly and secretion of recombinant human acetylcholinesterase" J. Biol. Chem. 266:23977–23984.

Wictorin et al., "Reformation of long axon pathways in adult rat CNS by human forebrain neuroblasts" *Nature*, 347:556–558 (1990).

Wagner, 1994. Gene inhibition using antisense oligodeoxynucleotides, Nature, 372:333.

Whitesell et al., 1991. Mol. Cell. Biol., 11:1360.

Woolf et al., 1990. Nucleic Acids Res., 18:1763–1769.

Soreq et al. (1990) "Molecular cloning and construction of the coding region for human acetylcholinesterase reveals a G,C rich attenuating structure" Proc. Natl. Acad. Sci. USA 87:9688–9692.

```
                            SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: other nucleic acid (iv) ANTI-SENSE: YES (xi) SEQUENCE DESCRIPTION: SEQ ID NO: 1:

ACGCTTTCTT GAGGC                                                           15

(2) INFORMATION FOR SEQ ID NO: 2:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: other nucleic acid (iv) ANTI-SENSE: YES (xi) SEQUENCE DESCRIPTION: SEQ ID NO: 2:

GGCACCCTGG GCAGC                                                           15

(2) INFORMATION FOR SEQ ID NO: 3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid (iv) ANTI-SENSE: YES (xi) SEQUENCE DESCRIPTION: SEQ ID NO: 3:

CCACGTCCTC CTGCACCGTC                                                      20

(2) INFORMATION FOR SEQ ID NO: 4:

(i) SEQUENCE CHARACTERISTICS:
          (A) LENGTH: 20 base pairs
          (B) TYPE: nucleic acid
          (C) STRANDEDNESS: single
          (D) TOPOLOGY: linear
```

(ii) MOLECULE TYPE: other nucleic acid (iv) ANTI-SENSE: YES (xi) SEQUENCE DESCRIPTION: SEQ ID NO: 4:

ATGAACTCGA TCTCGTAGCC                                                           20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 5:

GCCAGAGGAG GAGGAGAAGG                                                           20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 6:

TAGCGTCTAC CACCCCTGAC                                                           20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 7:

TCTGTGTTAT AGCCCAGCCC                                                           20

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 8:

GGCCTGTAAC AGTTTATTT                                                            19

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO: 9:

CTGCAATATT TTCTTGCACC                                                      20

(2) INFORMATION FOR SEQ ID NO: 10:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 10:

CGCGAAGCG                                                                   9

(2) INFORMATION FOR SEQ ID NO: 11:

(i) SEQUENCE CHARACTERISTICS:
            (A) LENGTH: 45 amino acids
            (B) TYPE: amino acid
            (C) STRANDEDNESS: not relevant
            (D) TOPOLOGY: not rele vant (ii) MOLECULE TYPE: peptide (iii) HYPOTHETICAL: NO (vi) ORIGINAL SOURCE:
            (A) ORGANISM: Homo sap iens (xi) SEQUENCE DESCRIPTION: SEQ ID NO: 11:

Leu Leu Ser Ala Thr Asp Thr Leu Asp Glu A la Glu Arg Gln Trp Lys
1               5                   10                  15

Ala Glu Phe His Arg Trp Ser Ser Tyr Met V al His Trp Lys Asn Gln
               20                  25                  30

Phe Asp His Tyr Ser Lys Gln Asp Arg Cys S er Asp Leu
       35                  40                  45

(2) INFORMATION FOR SEQ ID NO: 12:

(i) SEQUENCE CHARACTERISTICS:
            (A) LENGTH: 48 amino acids
            (B) TYPE: amino acid
            (C) STRANDEDNESS: not relevant
            (D) TOPOLOGY: not rele vant (ii) MOLECULE TYPE: peptide (iii) HYPOTHETICAL: NO (vi) ORIGINAL SOURCE:
            (A) ORGANISM: Homo sap iens (xi) SEQUENCE DESCRIPTION: SEQ ID NO: 12:

Leu Leu Ser Ala Thr Ala Ser Glu Ala Pro S er Thr Cys Pro Gly Phe
1               5                   10                  15

Thr His Gly Glu Ala Ala Pro Arg Pro Gly L eu Pro Leu Pro Leu Leu
               20                  25                  30

```
Leu Leu His Cys Leu Leu Leu Leu Phe Leu S er His Leu Arg Arg Leu
        35                  40                  45
```

(2) INFORMATION FOR SEQ ID NO: 13:

(i) SEQUENCE CHARACTERISTICS:
        (A) LENGTH: 31 amino acids
        (B) TYPE: amino acid
        (C) STRANDEDNESS: not relevant
        (D) TOPOLOGY: not rele vant (ii) MOLECULE TYPE: peptide (iii) HYPOTHETICAL: NO (vi) ORIGINAL SOURCE:
        (A) ORGANISM: Homo sap iens (xi) SEQUENCE DESCRIPTION: SEQ ID NO: 13:

```
Leu Leu Ser Ala Thr Gly Met Gln Gly Pro A la Gly Ser Gly Trp Glu
1           5                   10                  15

Glu Gly Ser Gly Ser Pro Pro Gly Val Thr P ro Leu Phe Ser Pro
            20                  25                  30
```

What is claimed is:

1. A method of treating injury to the central nervous system by administering to the central nervous system of a patient suffering from such an injury a therapeutically effective amount of an antisense oligonucleotide of acetylcholinesterase production immediately following the injury whereby acetylcholinesterase activity and production is downregulated.

2. The method as set forth in claim 1 wherein the injury to the central nervous system is a closed head injury.

3. The method as set forth in claim 1 wherein the injury to the central nervous system is a spinal cord trauma.

4. The method as set forth in claim 1 wherein the inhibitor of acetylcholinesterase production is a synthetic nuclease resistant antisense oligodeoxynucleotide or a ribozyme directed against an accessible domain of AChEmRMA synaptic or readthrough variants.

5. The method as set forth in claim 4 wherein the inhibitor is at least one synthetic nuclease resistant antisense oligodeoxynucleotide selected from the group consisting of 5'ACGCTTTCTTGAGGC 3' (SEQ ID No:1),
    5'GGCACCCTGGGCAGC 3' (SEQ ID No:2)
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

6. The method as set forth in claim 1 further including the inhibitor being administered a second time in case, following said first administration, monitoring of the patient by magnetic resonance imaging (MRI) shows that c-fos activity is still present.

7. A method of facilitating transplantation of neuronal cells to the central nervous system of a patient in need of such transplantation by by administering a therapeutically effective amount of an antisense oligonucleotide inhibitor of acethlcholinecterase production at the time of transplant.

8. The method as set forth in claim 7 wherein the neuronal cells to be transplanted are selected from the group consisting of neurons of fetal origin, neurons of adult origin and a neuronal cell line.

9. The method as set forth in claim 8 wherein the neuronal cells to be transplanted are genetically modified to produce a noncatalytic brain specific variant of acetylcholinesterase under control of an inducible promoter.

10. The method as set forth in claim 6 wherein the inhibitor is at least one synthetic nuclease resistant antisense oligodeoxynucleotide selected from the group consisting of 5'ACGCTTTCTTGAGGC 3' (SEQ ID No:1),
    5'GGCACCCTGGGCAGC 3' (SEQ ID No:2)
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

11. A pharmaceutical or medical composition for the treatment of injury to the central nervous system comprising as active ingredient at least one antisense oligonucleotide inhibitor of acetylcholinesterase production in a physiologically acceptable carrier or diluent for the treatment of injury to the central nervous system.

12. A pharmaceutical or medical composition wherein said inhibitor as set forth in claim 11 is a synthetic nuclease resistant antisense oligodeoxynucleotide directed against an accessible domain of an AChEmRNA brain variant.

13. A pharmaceutical or medical composition as set forth in claim 12 wherein said synthetic nuclease resistant antisense oligodeoxynucleotides are selected from the group consisting of 5'ACGCTTTCTTGAGGC 3' (SEQ ID No:1),
    5'GGCACCCTGGGCAGC 3' (SEQ ID No:2)
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

14. A method of making a synthetic nuclease resistant antisense oligodeoxynucleotide directed against an accessible domain of AChEmRNA synaptic or readthrough variants, said composition being intended for the treatment of injury to the central nervous system, said method comprising the step of combining the synthetic nuclease resistant antisense oligodeoxynucleotides with the physiologically acceptable carrier or diluent.

15. Use according to claim 14 wherein said antisense oligodeoxynucleotide is selected from the group consisting of 5'ACGCTTTCTTGAGGC 3' (SEQ ID No:1), 5'GGCACCCTGGGCAGC 3' (SEQ ID No:2)
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

16. A method of improving hippocampal neuron survival following injury to the central nervous system by administering to the central nervous system of a patient suffering from such an injury a therapeutically effective amount of an inhibitor of acetylcholinesterase production immediately following the injury.

17. The method as set forth in claim 16 wherein the injury to the central nervous system is a closed head injury.

18. The method as set forth in claim 16 wherein the inhibitor of acetylcholinesterase production is a synthetic nuclease resistant antisense oligodeoxynucleotide directed against an accessible domain of an AChEmRNA brain variant.

19. The method as set forth in claim 18 wherein the inhibitor is at least one synthetic nuclease resistant antisense oligodeoxynucleotide selected from the group consisting of 5'ACGCTTTCTTGAGGC 3' (SEQ ID No:1), 5'GGCACCCTGGGCAGC 3' (SEQ ID No:2)
    5'CCACGTCCTCCTGCACCGTC 3' (SEQ ID No:3),
    5'ATGAACTCGATCTCGTAGCC 3' (SEQ ID No:4),
    5'GCCAGAGGAGGAGGAGAAGG 3' (SEQ ID No:5),
    5'TAGCGTCTACCACCCCTGAC 3' (SEQ ID No:6),
    5'TCTGTGTTATAGCCCAGCCC 3' (SEQ ID No:7), and
    5'GGCCTGTAACAGTTTATTT 3' (SEQ ID No:8).

20. A method of making a synthetic nuclease resistant antisense oligodeoxynucleotides directed against an accessible domain of AChEmRNA synaptic or readthrough variants, said composition being intended for improving hippocampal neuron survival following injury to the central nervous system, said method comprising the step of combining the synthetic nuclease resistant antisense oligodeoxynucleotides with the physiologically acceptable carrier or diluent.

\* \* \* \* \*